US011279937B2

(12) United States Patent
Peralta-Yahya et al.

(10) Patent No.: US 11,279,937 B2
(45) Date of Patent: Mar. 22, 2022

(54) ENGINEERED THIOESTERASE MUTANTS AND METHODS OF USING SAME TO PRODUCE FATTY ACIDS

(71) Applicant: Georgia Tech Research Corporation, Atlanta, GA (US)

(72) Inventors: Pamela Peralta-Yahya, Atlanta, GA (US); Stephen Sarria, Atlanta, GA (US); Adam Verga, Atlanta, GA (US); Michael D. Burkart, San Diego, CA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 16/598,720

(22) Filed: Oct. 10, 2019

(65) Prior Publication Data

US 2020/0115714 A1 Apr. 16, 2020

Related U.S. Application Data

(60) Provisional application No. 62/743,820, filed on Oct. 10, 2018.

(51) Int. Cl.
*C12N 15/52* (2006.01)

(52) U.S. Cl.
CPC ...... *C12N 15/52* (2013.01); *C12Y 301/01093* (2015.07)

(58) Field of Classification Search
None
See application file for complete search history.

(56) References Cited

PUBLICATIONS

Chica et al. CurrOpin Biotechnol. Aug. 2005;16(4):378-84. (Year: 2005).*
Singh et al. Curr Protein Pept Sci. 2017, 18, 1-11 (Year: 2017).*
Zheng et al. Biotechnology for Biofuels 2012, 5:76, pp. 1-12 (Year: 2012).*
Zhang et al. Journal of Lipid Research, vol. 44, Issue 1, Jan. 2003, pp. 1-10 (Year: 2003).*
Kozakov et al. How good is automated protein docking? Proteins. Dec. 2013; 81(12): 2159-2166 (Year: 2013).*
Grisewood et al. ACS Catal. 2017, 7, 6, 3837-3849. Publication Date:Apr. 20, 2017 (Year: 2017).*
Bornscheuer et al. Curr Protoc Protein Sci. Nov. 2011;Chapter 26:Unit26.7. (Year: 2011).*
Li et al. Biotechnol Bioeng. Jul. 2014;111(7):1273-87. Epub May 6, 2014. (Year: 2014).*
Sarria et al. ACS Synth. Biol. 2018, 7, 1179-1187. Epub May 3, 2018. (Year: 2018).*

* cited by examiner

*Primary Examiner* — Christian L Fronda
(74) *Attorney, Agent, or Firm* — Troutman Pepper Hamilton Sanders LLP; Ryan A. Schneider

(57) ABSTRACT

The disclosure is directed to a method of engineering a heterologous thioesterase (TE) enzyme to interact with endogenous acyl-ACP proteins in order to produce molecules of interest in a bacterial host. The method can identify amino acids at the binding interface between the heterologous TE and the endogenous acyl-ACP that can be substituted so that the heterologous TE can better interact with the endogenous acyl-ACP. Mutant heterologous TE enzymes with improved interactions with the endogenous acyl-ACP are also provided.

8 Claims, 9 Drawing Sheets

Specification includes a Sequence Listing.

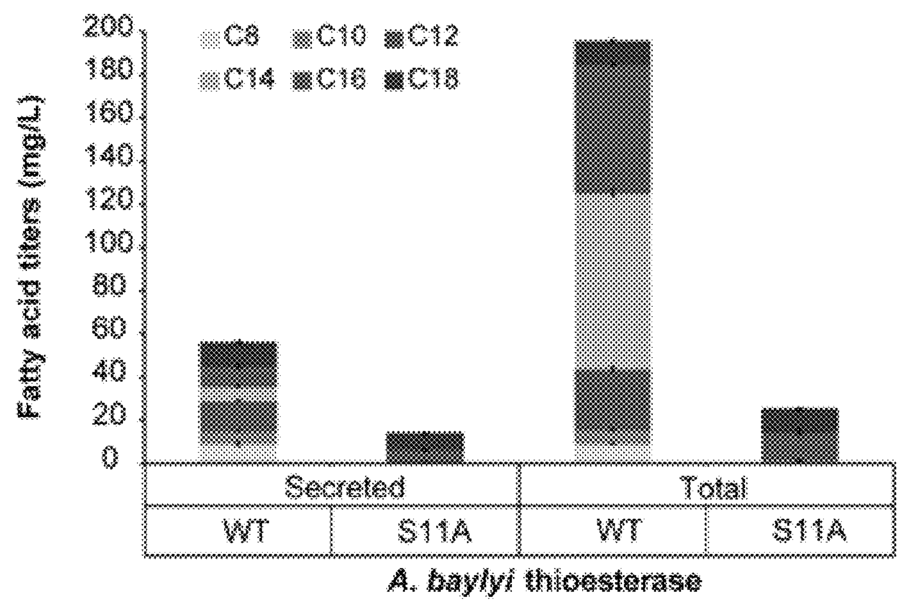
Figure 2C
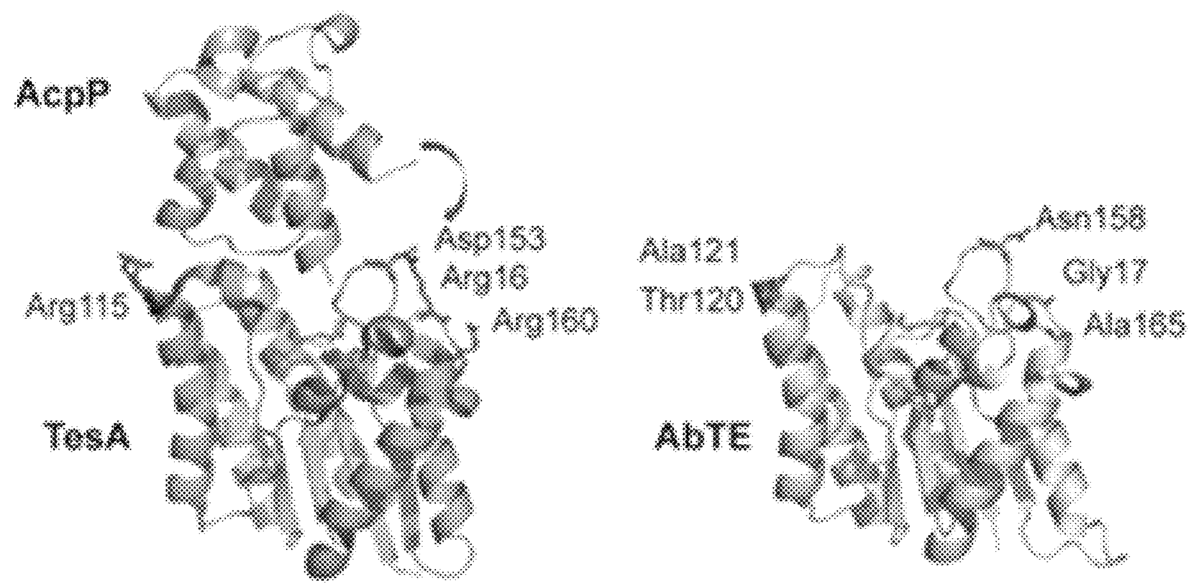
Figure 2D
Figure 2E

ENGINEERED THIOESTERASE MUTANTS AND METHODS OF USING SAME TO PRODUCE FATTY ACIDS

CROSS-REFERENCE TO RELATED APPLICATIONS

This application claims priority to U.S. Provisional Application No. 62/743,820, filed on 10 Oct. 2018, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Oct. 3, 2019, is named GTRC7595_011529_113444_SL.txt and is 57,460 bytes in size.

BACKGROUND OF THE DISCLOSURE

1. Field of the Disclosure

Embodiments of the present disclosure relate generally to modifying amino acids at the interface between interacting enzymes in order to alter their binding, and more specifically to engineering the interacting surface of heterologous thioesterase (TE) enzymes to improve binding to endogenous host fatty acyl-acyl carrier proteins (fatty acyl-ACPs).

2. Background

The introduction of heterologous proteins into a host cell faces numerous hurdles, from proper expression of the protein to proper folding to proper function in the host cell. When introducing a heterologous protein that is intended to interact with an endogenous host protein, amino acids at the surface of the heterologous protein may need to be substituted in order to improve the interaction while maintaining the protein's function.

Heterologous proteins are often introduced into bacterial cells to express molecules of interest. Many times, these molecules are either not produced at all by the bacteria or are produced in low amounts. For example, microbial production of medium-chain fatty acids (MCFAs; includes C8-C12 backbones) is limited by the activity and product profile of bacterial enzymes, specifically bacterial acyl-ACP thioesterases. MCFAs are useful as antimicrobials and emulsifying agents and can be derivatized to form a number of useful chemical intermediates (e.g., alkenes, α-olefins, esters, alcohols, ketones, hydroxyacids such as w-hydroxycarboxylic acids, and dicarboxylic acids such as α,α-dicarboxylic acids).

Previous attempts to synthesize MCFAs in bacteria included providing plant thioesterases (TEs) that were not efficiently expressed in the host as well as mutagenizing amino acids near the active site of bacterial TEs in an attempt to change the fatty acids produced by the enzymes to MCFAs. For example, the TE that interacts with AcpP in *E. coli*, TesA, has frequently been mutagenized near its active site in order to improve MCFA production without much success.

What is needed, therefore, is a method of engineering a heterologous thioesterase enzyme to interact with endogenous acyl-ACP proteins in order to produce molecules of interest in a bacterial host. The method should identify amino acids at the binding interface between the heterologous TE and the endogenous acyl-ACP that can be substituted so that the heterologous TE can better interact with the endogenous acyl-ACP. Mutant heterologous TE enzymes with improved interactions with the endogenous acyl-ACP are also provided. It is to such a method that embodiments of the present disclosure are directed.

BRIEF SUMMARY OF THE DISCLOSURE

As specified in the Background Section, there is a great need in the art to identify technologies for protein engineering and use this understanding to develop novel methods of engineering heterologous enzymes to interact with endogenous proteins in order to produce molecules of interest in a bacterial host. The present disclosure satisfies this and other needs. Embodiments of the present disclosure relate generally to modifying amino acids at the interface between interacting enzymes in order to alter their binding, and more specifically to engineering the interacting surface of heterologous thioesterase enzymes to improve binding to endogenous host acyl-ACP proteins.

In one aspect, the disclosure provides a method for generating a thioesterase mutant comprising: selecting a heterologous thioesterase for mutation based at least in part on a desired end product that is produced by the heterologous thioesterase; identifying amino acids on the heterologous thioesterase that form an interacting surface with *E. coli* AcpP and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell.

In another aspect, the disclosure provides a heterologous thioesterase mutant produced by a method comprising: identifying a heterologous thioesterase for mutation based at least in part on a desired end product that is produced by the heterologous thioesterase; identifying amino acids in the heterologous thioesterase amino acid sequence that form an interacting surface with an *E. coli* AcpP protein and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell.

These and other objects, features and advantages of the present disclosure will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below. The patent or application file contains at least one drawing executed in color. Copies of this patent or patent application publication with color drawing(s) will be provided by the Office upon request and payment of the necessary fee.

(FIG. 1A) *E. coli* Type II fatty acid synthase (FAS) extends and reduces an acyl chain bound to acyl-carrier protein (ACP). All enzymes in FAS interact with ACP. Thioesterases (TEs) hydrolyze acyl-ACPs to free fatty acids of different chain lengths according to their substrate specificity. (FIG. 1B) Matching the surface interface between the native *E. coli* AcpP and heterologous medium-chain *Acinetobacter baylyi* TE (AbTE), improves medium-chain fatty acid production in *E. coli.*

FIGS. 2A-2E depict medium-chain fatty acid production and calculated *E. coli* AcpP interphase with TEs. (FIG. 2A) Secreted fatty acid titers of *E. coli* (MG1655) expressing four heterologous TEs. (FIG. 2B) Secreted fatty acid titers by different *E. coli* strains expressing *A. baylyi* TE (AbTE: WT). (FIG. 2C) Secreted and total (secreted plus intracellular and membrane bound) fatty acid titers produced by *E. coli* expressing AbTE:WT and inactive AbTE (AbTE: S11A). The experiments were done in triplicate and the error bars represent the standard deviation from the mean. (FIG. 2D) Docking of *E. coli* AcpP (magenta, PDB ID: 1FAE) and *E. coli* 'TesA (cyan, PDB ID 1U8U) identifies potential residues on the 'TesA surface that are important for interactions between 'TesA and AcpP. (FIG. 2E) Homology model of AbTE with surface residues equivalent to 'TesA labelled.

(FIG. 4A) Secreted fatty acid levels of *E. coli* expressing AbTE single, double, and triple arginine mutants, as well as AbTE single and double glutamate mutants. All experiments were done in triplicate and the error bars represent the standard deviation from the mean. (FIG. 4B) Time course of saturated fatty acid titers produced by *E. coli* expressing AbTE, AbTE:G17R, and AbTE:G17R/A165R. (FIG. 4C) Coomassie stained SDS-PAGE gel of Serial dilution of induced *E. coli* cultures expressing AbTE:WT, AbTE:G17R and AbTE:G17R/A165R.

FIG. 5A, AbTE:S11A (inactive enzyme); FIG. 5B, Wild-type AbTE; FIG. 5C, AbTE:G17R; FIG. 5D, AbTE: G17R/A165R. Single Ion Monitoring: 74 and 87.

DETAILED DESCRIPTION OF THE DISCLOSURE

Figure 1A:
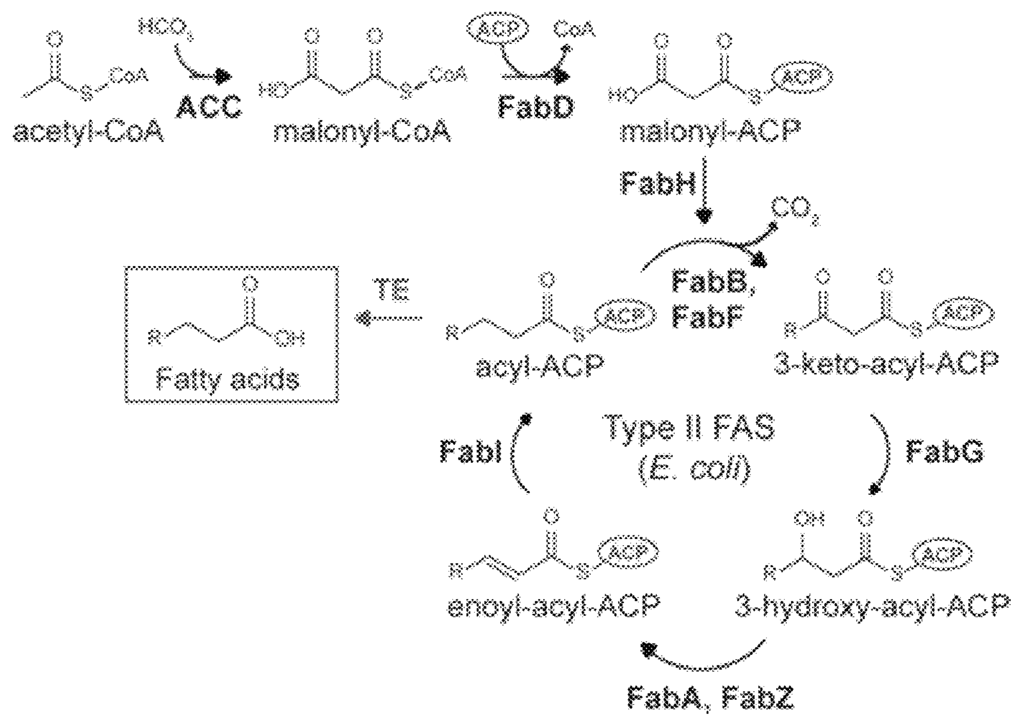
FIGS. 1A-1B depict the process of medium-chain fatty acid biosynthesis in *Escherichia coli*.

As specified in the Background Section, there is a great need in the art to identify technologies for protein engineering and use this understanding to develop novel methods of engineering heterologous enzymes to interact with endogenous proteins in order to produce molecules of interest in a bacterial host. The present disclosure satisfies this and other needs. Embodiments of the present disclosure relate generally to modifying amino acids at the interface between interacting enzymes in order to alter their binding, and more specifically to engineering the interacting surface of heterologous thioesterase enzymes to improve binding to endogenous host acyl-ACP proteins.

An exemplary application of this method, discussed in more detail below, involves the use of a natural medium-chain acyl-ACP TE as the engineering starting point in order to generate a TE variant with an almost exclusive MCFA product profile, potentially leading to higher MCFA yields. This TE variant has improved interaction with *E. coli* AcpP, which is an endogenous ACP carrier protein bound to a fatty acyl chain and is involved in fatty acid metabolism.

Definitions

To facilitate an understanding of the principles and features of the various embodiments of the disclosure, various illustrative embodiments are explained below. Although exemplary embodiments of the disclosure are explained in detail, it is to be understood that other embodiments are contemplated. Accordingly, it is not intended that the disclosure is limited in its scope to the details of construction and arrangement of components set forth in the following description or examples. The disclosure is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to +20%, preferably up to +10%, more preferably up to +5%, and more preferably still up to +1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value. Throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present disclosure are intended to be illustrative and not restrictive. Many suitable materials that would perform the same or a similar function as the materials described herein are intended to be embraced within the scope of the disclosure. Such other materials not described herein can include, but are not limited to, materials that are developed after the time of the development of the disclosure, for example. Any dimensions listed in the various drawings are for illustrative purposes only and are not intended to be limiting. Other dimensions and proportions are contemplated and intended to be included within the scope of the disclosure.

The term "expression" as used herein is defined as the transcription and/or translation of a particular nucleotide sequence driven by its promoter.

A "vector" as used herein is a DNA molecule used as a vehicle to artificially carry foreign genetic material into another cell by transfection, transformation, or transduction, where it can be replicated and/or expressed (e.g., plasmids, cosmids, phages, viral vectors, expression vectors).

The terms "sequence identity" and "percent identity" are used interchangeably herein. For the purpose of this disclosure, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

Several different computer programs are available to determine the degree of identity between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accelrys.com/products/gcg), using either a Blosum 62 matrix or a PAM250 matrix, and a gap weight of 16, 14, 12, 10, 8, 6, or 4 and a length weight of 1, 2, 3, 4, 5, or 6. These different parameters will yield slightly different results but the overall percentage identity of two sequences is not significantly altered when using different algorithms.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95%, e.g., at least 96%, 97%, 98%, 99%, or 100% "sequence identity" to a reference nucleotide sequence, it is intended that the nucleotide sequence of the given polynucleotide is identical to the reference sequence except that the given polynucleotide sequence may include up to 5, 4, 3, 2, 1, or 0 point mutations per each 100 nucleotides of the reference nucleotide sequence. In other words, in a polynucleotide having a nucleotide sequence having at least 95%, e.g., at least 96%, 97%, 98%, 99%, or 100% sequence identity relative to the reference nucleotide sequence, up to 5%, 4%, 3%, 2%, 1%, or 0% of the nucleotides in the reference sequence may be deleted or substituted with another nucleotide, or a number of nucleotides up to 5%, 4%, 3%, 2%, 1%, or 0% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95%, e.g., at least 96%, 97%, 98%, 99%, or 100% sequence identity to a reference amino acid sequence, it is intended that the given amino acid sequence of the polypeptide is identical to the reference sequence except that the given polypeptide sequence may include up to 5, 4, 3, 2, 1, or 0 amino acid alterations per each 100 amino acids of the reference amino acid sequence. In other words, to obtain a given polypeptide sequence having at least 95%, e.g., at least 96%, 97%, 98%, 99%, or 100% sequence identity with a reference amino acid sequence, up to 5%, 4%, 3%, 2%, 1%, or 0% of the amino acid residues in the reference sequence may be deleted or substituted with another amino acid, or a number of amino acids up to 5%, 4%, 3%, 2%, 1%, or 0% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "variant" of a polypeptide according to the present disclosure may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present disclosure, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical*

*Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); Transcription and Translation (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Methods of the Disclosure

In one aspect, the disclosure provides methods of selectively mutating heterologous thioesterase enzymes to improve their interaction with endogenous fatty acyl-acyl carrier proteins.

In one aspect, the disclosure provides a method for generating a thioesterase mutant comprising: selecting a heterologous thioesterase for mutation by selecting a desired end product that is produced by the heterologous thioesterase; identifying amino acids on the heterologous thioesterase that form an interacting surface with an endogenous fatty acyl-acyl carrier protein and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell.

In another aspect, the disclosure provides a method for generating a thioesterase mutant comprising: selecting a heterologous thioesterase for mutation by selecting a desired end product that is produced by the heterologous thioesterase; identifying amino acids on the heterologous thioesterase that form an interacting surface with *E. coli* AcpP and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell.

In any of the foregoing aspects, the method can further comprise one or more of the following embodiments. Each combination is specifically contemplated herein.

In any of the embodiments disclosed herein, the desired end product can comprise medium-chain fatty acids, long-chain fatty acids, short-chain fatty acids, and branched fatty acids. In any of the embodiments disclosed herein, the heterologous thioesterase produces medium-chain fatty acids.

In any of the embodiments disclosed herein, the heterologous thioesterase can comprise a mammalian thioesterase, a diatom thioesterase, a plant thioesterase, an algal thioesterase, and a heterologous bacterial thioesterase. In any of the embodiments disclosed herein, the heterologous thioesterase can comprise a thioesterase from *Acinetobacter baylyi*.

In any of the embodiments disclosed herein, the step of identifying the amino acids in the interacting surface can comprise one or more of: performing modeling to identify amino acids in an interacting surface between the endogenous fatty acyl-acyl carrier protein and an endogenous thioesterase protein; performing structural homology modeling to align the heterologous thioesterase amino acid sequence with the endogenous thioesterase amino acid sequence to identify a corresponding interacting surface on the heterologous thioesterase amino acid sequence; and performing modeling to identify amino acids in an interacting surface between the endogenous fatty acyl-acyl carrier protein and the heterologous thioesterase protein.

In any of the embodiments disclosed herein, the step of identifying amino acids suitable for mutation can comprise: determining an interaction between the endogenous thioesterase and the endogenous fatty acyl-acyl carrier protein; identifying corresponding amino acid positions on the heterologous thioesterase via the structural homology modeling with the endogenous thioesterase; and determining which amino acid substitutions in the heterologous thioesterase will result in a similar interaction with the endogenous fatty acyl-acyl carrier protein.

In any of the embodiments disclosed herein, the interaction is selected from the group consisting of covalent bonds and non-covalent bonds. In any of the embodiments disclosed herein, the covalent bonds can comprise disulfide bridges. In any of the embodiments disclosed herein, the non-covalent bonds can comprise electrostatic interactions, Van der Waals forces, hydrogen bonds and hydrophobic bonds.

In any of the embodiments disclosed herein, the step of mutagenizing the identified amino acids can be performed by site-directed mutagenesis, site saturation mutagenesis, loop swapping mutagenesis, and CRISPR mutagenesis (see, e.g., Jakociunas et al., CasPER, a method for directed evolution in genomic contexts using mutagenesis and CRISPR/Cas9, Metabolic Engineering Volume 48, July 2018, p. 288-296).

In any of the embodiments disclosed herein, the step of expressing the nucleic acid comprising the mutated heterologous thioesterase nucleotide sequence can comprise: cloning the nucleic acid comprising the mutated heterologous thioesterase nucleotide sequence into an expression vector; transforming the expression vector into an appropriate bacterial host; inducing expression of the mutated heterologous thioesterase protein; and analyzing an amount or purity of the end product produced by the mutated heterologous thioesterase protein.

In any of the embodiments disclosed herein, the method can further comprise: identifying heterologous thioesterase mutants that yield a high amount of the end product and/or a high purity of the end product; and introducing those substitutions into a nucleic acid comprising the heterologous thioesterase nucleotide sequence to provide a multiple mutant thioesterase nucleotide sequence.

In any of the embodiments disclosed herein, the method can involve expression of the mutated heterologous thioesterase in a bacterial cell. In any of the embodiments disclosed herein, the bacterial cell can be an *E. coli* cell. In any of the embodiments disclosed herein, the *E. coli* cell can be from the DH5alpha, BL21, DH10B, MG1655 or BW25113 strains.

In any of the embodiments described herein, the method can further comprise detecting the end product. In any of the embodiments described herein, the end product can be detected by a variety of methods including but not limited to gas chromatography mass spectrometry, liquid chromatography mass spectrometry, or a biosensor (e.g., the biosensor described in U.S. Patent Pub. No. 2016/0122832).

In another aspect, the disclosure provides a method for generating a thioesterase mutant comprising: selecting a heterologous thioesterase for mutation by selecting a desired end product that is produced by the heterologous thioesterase; identifying amino acids on the heterologous thioesterase that form an interacting surface with *E. coli* AcpP and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell.

In any of the foregoing aspects, the method can further comprise one or more of the following embodiments. Each combination is specifically contemplated herein.

In any of the embodiments disclosed herein, the desired end product can comprise medium-chain fatty acids, long-chain fatty acids, short-chain fatty acids, and branched fatty acids. In any of the embodiments disclosed herein, the heterologous thioesterase produces medium-chain fatty acids.

In any of the embodiments disclosed herein, the heterologous thioesterase can comprise a mammalian thioesterase, a diatom thioesterase, a plant thioesterase, an algal thioesterase, and a heterologous bacterial thioesterase. In any of the embodiments disclosed herein, the heterologous thioesterase can comprise a thioesterase from *Acinetobacter baylyi*.

In any of the embodiments disclosed herein, the step of identifying the interacting surface can comprise one or more of: performing modeling to identify amino acids in an interacting surface between the AcpP protein and an endogenous thioesterase protein; performing structural homology modeling to align the heterologous thioesterase amino acid sequence with the AcpP amino acid sequence to identify a corresponding interacting surface on the heterologous thioesterase amino acid sequence; and performing modeling to identify amino acids in an interacting surface between the AcpP protein and the heterologous thioesterase protein.

In any of the embodiments disclosed herein, the step of identifying amino acids suitable for mutation can comprise: determining an interaction between the endogenous thioesterase and the AcpP protein; identifying corresponding amino acid positions on the heterologous thioesterase via the structural homology modeling with the endogenous thioesterase; and determining which amino acid substitutions in the heterologous thioesterase will result in a similar interaction with the AcpP protein.

In any of the embodiments disclosed herein, the interaction is selected from the group consisting of covalent bonds and non-covalent bonds. In any of the embodiments disclosed herein, the covalent bonds can comprise disulfide bridges. In any of the embodiments disclosed herein, the non-covalent bonds can comprise electrostatic interactions, Van der Waals forces, hydrogen bonds and hydrophobic bonds.

In any of the embodiments disclosed herein, the step of mutagenizing the identified amino acids can be performed by site-directed mutagenesis, site saturation mutagenesis, loop swapping mutagenesis, and CRISPR mutagenesis (see, e.g., Jakociunas et al., CasPER, a method for directed evolution in genomic contexts using mutagenesis and CRISPR/Cas9, Metabolic Engineering Volume 48, July 2018, p. 288-296).

In any of the embodiments disclosed herein, the step of expressing the nucleic acid comprising the mutated heterologous thioesterase nucleotide sequence can comprise: cloning the nucleic acid comprising the mutated heterologous thioesterase nucleotide sequence into an expression vector; transforming the expression vector into an appropriate bacterial host; inducing expression of the mutated heterologous thioesterase protein; and analyzing an amount or purity of the end product produced by the mutated heterologous thioesterase protein.

In any of the embodiments disclosed herein, the method can further comprise: identifying heterologous thioesterase mutants that yield a high amount of the end product and/or a high purity of the end product; and introducing those substitutions into a nucleic acid comprising the heterologous thioesterase nucleotide sequence to provide a multiple mutant thioesterase nucleotide sequence.

In any of the embodiments disclosed herein, the heterologous thioesterase can be an *Acinetobacter* thioesterase. In any of the embodiments disclosed herein, the heterologous thioesterase can be an *Acinetobacter baylyi* thioesterase. In any of the embodiments disclosed herein, the heterologous thioesterase can be an *Acinetobacter baylyi* acyl-ACP thioesterase. In any of the embodiments disclosed herein, the heterologous thioesterase can have a DNA sequence comprising the nucleotide sequence of SEQ ID NO 1. In any of the embodiments disclosed herein, the heterologous thioesterase can have an amino acid sequence comprising the amino acid sequence of SEQ ID NO 2. In any of the embodiments disclosed herein, the heterologous thioesterase can have a DNA sequence that is at least 90%, 91%, 92%, 93%, 94%, 95%, 96%, 97%, 98%, or 99% identical to the nucleotide sequence of SEQ ID NO 1. In any of the embodiments disclosed herein, the heterologous thioesterase can have an amino acid sequence that is at least 90%, 91%, 92%, 93%, 94%, 95%, 96%, 97%, 98%, or 99% identical to the amino acid sequence of SEQ ID NO 2.

In any of the embodiments disclosed herein, the thioesterase mutant can comprise a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In any of the embodiments disclosed herein, the thioesterase mutant can comprise an amino acid sequence selected from the group consisting of SEQ ID NOs 9, 11, 13, 15, 17, 19, 21, 23, 25, 27, 29, 31, 33, 35, 37, 39, 41, 43, and combinations thereof. In any of the embodiments disclosed herein, the thioesterase mutant can comprise a nucleic acid sequence that is at least 90%, 91%, 92%, 93%, 94%, 95%, 96%, 97%, 98%, or 99% identical to a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In any of the embodiments disclosed herein, the thioesterase mutant can comprise an amino acid sequence that is at least 90%, 91%, 92%, 93%, 94%, 95%, 96%, 97%, 98%, or 99% identical to an amino acid sequence selected from the group consisting of SEQ ID NOs 9, 11, 13, 15, 17, 19, 21, 23, 25, 27, 29, 31, 33, 35, 37, 39, 41, 43, and combinations thereof.

In a related aspect, the disclosure provides a nucleic acid comprising any thioesterase mutant nucleotide sequence as described herein. In a related aspect, the disclosure provides an amino acid sequence comprising any mutant amino acid sequence as described herein. In a related aspect, the disclosure provides a nucleic acid sequence that is at least 90%, 91%, 92%, 93%, 94%, 95%, 96%, 97%, 98%, or 99% identical to a nucleic acid comprising any thioesterase mutant nucleotide sequence as described herein. In a related aspect, the disclosure provides an amino acid sequence that is at least 90%, 91%, 92%, 93%, 94%, 95%, 96%, 97%, 98%, or 99% identical to an amino acid sequence comprising any thioesterase mutant amino acid sequence as described herein.

In a related aspect, the disclosure provides a vector comprising any nucleic acid or any thioesterase mutant nucleotide sequence as described herein.

In a related aspect, the disclosure provides a bacterial cell comprising any vector as described herein. In a related aspect, the disclosure provides a bacterial cell comprising any nucleic acid as described herein. In a related aspect, the disclosure provides a bacterial cell comprising any thioesterase mutant nucleotide sequence as described herein. In a related aspect, the disclosure provides an *E. coli* cell comprising any vector as described herein. In a related aspect, the disclosure provides an *E. coli* cell comprising any nucleic acid as described herein. In a related aspect, the disclosure provides an *E. coli* cell comprising any thioesterase mutant nucleotide sequence as described herein.

In any of the embodiments disclosed herein, the bacterial cell can be an *E. coli* cell. In any of the embodiments disclosed herein, the *E. coli* cell can be from the DH5alpha, BL21, DH10B, MG1655 or BW25113 strains.

In any of the embodiments described herein, the method can further comprise detecting the end product. In any of the embodiments described herein, the end product can be detected by a variety of methods including but not limited to gas chromatography mass spectrometry, liquid chromatography mass spectrometry, or a biosensor (e.g., the biosensor described in U.S. Patent Pub. No. 2016/0122832).

Compositions of the Disclosure

In another aspect, the disclosure provides mutated heterologous thioesterase enzymes that are capable of improved interactions with endogenous fatty acyl-acyl carrier proteins.

In another aspect, the disclosure provides a heterologous thioesterase mutant produced by a method comprising: selecting a heterologous thioesterase for mutation by selecting a desired end product that is produced by the heterologous thioesterase; identifying amino acids on the heterologous thioesterase that form an interacting surface with an endogenous fatty acyl-acyl carrier protein and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase in a bacterial cell.

In any of the foregoing aspects, the method can further comprise one or more of the following embodiments. Each combination is specifically contemplated herein.

In any of the embodiments disclosed herein, the desired end product can comprise medium-chain fatty acids, long-chain fatty acids, short-chain fatty acids, and branched fatty acids. In any of the embodiments disclosed herein, the heterologous thioesterase can produce medium-chain fatty acids.

In any of the embodiments disclosed herein, the heterologous thioesterase can comprise a mammalian thioesterase, a diatom thioesterase, a plant thioesterase, an algal thioesterase, and a heterologous bacterial thioesterase. In any of the embodiments disclosed herein, the heterologous thioesterase can comprise a thioesterase from *Acinetobacter baylyi*.

In any of the embodiments disclosed herein, the step of identifying the interacting surface can comprise one or more of: performing modeling to identify amino acids in an interacting surface between the endogenous fatty acyl-acyl carrier protein and an endogenous thioesterase; performing structural homology modeling to align the heterologous thioesterase with the endogenous thioesterase to identify a corresponding interacting surface on the heterologous thioesterase; and performing modeling to identify amino acids in an interacting surface between the endogenous fatty acyl-acyl carrier protein and the heterologous thioesterase.

In any of the embodiments disclosed herein, the step of identifying amino acids suitable for mutation can comprise: determining an interaction between the endogenous thioesterase and the endogenous fatty acyl-acyl carrier protein; identifying corresponding amino acid positions on the heterologous thioesterase via the structural homology modeling with the endogenous thioesterase; and determining which amino acid substitutions in the heterologous thioesterase will result in a similar interaction with the endogenous fatty acyl-acyl carrier protein.

In any of the embodiments disclosed herein, the interaction is selected from the group consisting of covalent bonds and non-covalent bonds. In any of the embodiments disclosed herein, the covalent bonds can comprise disulfide bridges. In any of the embodiments disclosed herein, the non-covalent bonds can comprise electrostatic interactions, Van der Waals forces, hydrogen bonds and hydrophobic bonds.

In any of the embodiments disclosed herein, the step of mutagenizing the identified amino acids is performed by site-directed mutagenesis, site saturation mutagenesis, loop swapping mutagenesis, and CRISPR mutagenesis (see, e.g., Jakociunas et al., CasPER, a method for directed evolution in genomic contexts using mutagenesis and CRISPR/Cas9, Metabolic Engineering Volume 48, July 2018, p. 288-296).

In any of the embodiments disclosed herein, the step of expressing the nucleic acid comprising the mutated heterologous thioesterase nucleotide sequence can comprise: cloning the nucleic acid comprising the mutated thioesterase nucleotide sequence into an expression vector; transforming the expression vector into an appropriate bacterial host; inducing expression of the mutated thioesterase protein; and analyzing an amount or purity of the end product produced by the mutated thioesterase protein.

In any of the embodiments disclosed herein, generation of the thioesterase mutant can further comprise: identifying thioesterase mutants that yield a high amount of the end product and/or a high purity of the end product; and introducing those substitutions into a nucleic acid comprising the heterologous thioesterase nucleotide sequence to provide a multiple mutant thioesterase nucleotide sequence.

In any of the embodiments disclosed herein, the bacterial cell can be an *E. coli* cell. In any of the embodiments disclosed herein, the *E. coli* cell can be from the DH5alpha, BL21, DH10B, MG1655 or BW25113 strains.

In any of the embodiments described herein, the method can further comprise detecting the end product. In any of the embodiments described herein, the end product can be detected by a variety of methods including but not limited to gas chromatography mass spectrometry, liquid chromatography mass spectrometry, or a biosensor (e.g., the biosensor described in U.S. Patent Pub. No. 2016/0122832).

In another aspect, the disclosure provides a heterologous thioesterase mutant produced by a method comprising: selecting a heterologous thioesterase for mutation by selecting a desired end product that is produced by the heterologous thioesterase; identifying amino acids on the heterologous thioesterase that form an interacting surface with an *E. coli* AcpP protein and are suitable for mutation; mutagenizing the identified amino acids of the heterologous thioesterase by introducing substitutions into a nucleic acid comprising the heterologous thioesterase nucleotide sequence; and expressing the nucleic acid comprising the mutated heterologous thioesterase in a bacterial cell.

In any of the foregoing aspects, the method can further comprise one or more of the following embodiments. Each combination is specifically contemplated herein.

In any of the embodiments disclosed herein, the desired end product can comprise medium-chain fatty acids, long-chain fatty acids, short-chain fatty acids, and branched fatty acids. In any of the embodiments disclosed herein, the heterologous thioesterase can produce medium-chain fatty acids.

In any of the embodiments disclosed herein, the heterologous thioesterase can comprise a mammalian thioesterase, a diatom thioesterase, a plant thioesterase, an algal thioesterase, and a heterologous bacterial thioesterase. In any of the embodiments disclosed herein, the heterologous thioesterase can comprise a thioesterase from *Acinetobacter baylyi*.

In any of the embodiments disclosed herein, the step of identifying the interacting surface can comprise one or more of: performing modeling to identify amino acids in an interacting surface between the AcpP protein and an endogenous thioesterase; performing structural homology modeling to align the heterologous thioesterase with the endogenous thioesterase to identify a corresponding interacting surface on the heterologous thioesterase; and performing modeling to identify amino acids in an interacting surface between the AcpP protein and the heterologous thioesterase.

In any of the embodiments disclosed herein, the step of identifying amino acids suitable for mutation can comprise: determining an interaction between the endogenous thioesterase and the AcpP protein; identifying corresponding amino acid positions on the heterologous thioesterase via the structural homology modeling with the endogenous thioesterase; and determining which amino acid substitutions in the heterologous thioesterase will result in a similar interaction with the AcpP protein.

In any of the embodiments disclosed herein, the interaction is selected from the group consisting of covalent bonds and non-covalent bonds. In any of the embodiments disclosed herein, the covalent bonds can comprise disulfide bridges. In any of the embodiments disclosed herein, the non-covalent bonds can comprise electrostatic interactions, Van der Waals forces, hydrogen bonds and hydrophobic bonds.

In any of the embodiments disclosed herein, the step of mutagenizing the identified amino acids is performed by site-directed mutagenesis, site saturation mutagenesis, loop swapping mutagenesis, and CRISPR mutagenesis (see, e.g., Jakociunas et al., CasPER, a method for directed evolution in genomic contexts using mutagenesis and CRISPR/Cas9, Metabolic Engineering Volume 48, July 2018, p. 288-296).

In any of the embodiments disclosed herein, the step of expressing the nucleic acid comprising the mutated heterologous thioesterase nucleotide sequence can comprise: cloning the nucleic acid comprising the mutated thioesterase nucleotide sequence into an expression vector; transforming the expression vector into an appropriate bacterial host; inducing expression of the mutated thioesterase protein; and analyzing an amount or purity of the end product produced by the mutated thioesterase protein.

In any of the embodiments disclosed herein, generation of the thioesterase mutant can further comprise: identifying thioesterase mutants that yield a high amount of the end product and/or a high purity of the end product; and introducing those substitutions into a nucleic acid comprising the heterologous thioesterase nucleotide sequence to provide a multiple mutant thioesterase nucleotide sequence.

In any of the embodiments disclosed herein, the heterologous thioesterase can be an *Acinetobacter* thioesterase. In any of the embodiments disclosed herein, the heterologous thioesterase can be an *Acinetobacter baylyi* thioesterase. In any of the embodiments disclosed herein, the heterologous thioesterase can be an *Acinetobacter baylyi* acyl-ACP thioesterase. In any of the embodiments disclosed herein, the heterologous thioesterase can have a DNA sequence comprising the nucleotide sequence of SEQ ID NO 1. In any of the embodiments disclosed herein, the heterologous thioesterase can have an amino acid sequence comprising the amino acid sequence of SEQ ID NO 2. In any of the embodiments disclosed herein, the heterologous thioesterase can have a DNA sequence that is at least 90%, 91%, 92%, 93%, 94%, 95%, 96%, 97%, 98%, or 99% identical to the nucleotide sequence of SEQ ID NO 1. In any of the embodiments disclosed herein, the heterologous thioesterase can have an amino acid sequence that is at least 90%, 91%, 92%, 93%, 94%, 95%, 96%, 97%, 98%, or 99% identical to the amino acid sequence of SEQ ID NO 2.

In any of the embodiments disclosed herein, the thioesterase mutant can comprise a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In any of the embodiments disclosed herein, the thioesterase mutant can comprise an amino acid sequence selected from the group consisting of SEQ ID NOs 9, 11, 13, 15, 17, 19, 21, 23, 25, 27, 29, 31, 33, 35, 37, 39, 41, 43, and combinations thereof. In any of the embodiments disclosed herein, the thioesterase mutant can comprise a nucleic acid sequence that is at least 90%, 91%, 92%, 93%, 94%, 95%, 96%, 97%, 98%, or 99% identical to a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In any of the embodiments disclosed herein, the thioesterase mutant can comprise an amino acid sequence that is at least 90%, 91%, 92%, 93%, 94%, 95%, 96%, 97%, 98%, or 99% identical to an amino acid sequence selected from the group consisting of SEQ ID NOs 9, 11, 13, 15, 17, 19, 21, 23, 25, 27, 29, 31, 33, 35, 37, 39, 41, 43, and combinations thereof.

In a related aspect, the disclosure provides a nucleic acid comprising any thioesterase mutant nucleotide sequence as described herein. In a related aspect, the disclosure provides an amino acid sequence comprising any mutant amino acid sequence as described herein. In a related aspect, the disclosure provides a nucleic acid sequence that is at least 90%, 91%, 92%, 93%, 94%, 95%, 96%, 97%, 98%, or 99% identical to a nucleic acid comprising any thioesterase mutant nucleotide sequence as described herein. In a related aspect, the disclosure provides an amino acid sequence that is at least 90%, 91%, 92%, 93%, 94%, 95%, 96%, 97%, 98%, or 99% identical to an amino acid sequence comprising any thioesterase mutant amino acid sequence as described herein. In a related aspect, the disclosure provides a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In a related aspect, the disclosure provides an amino acid sequence selected from the group consisting of SEQ ID NOs 9, 11, 13, 15, 17, 19, 21, 23, 25, 27, 29, 31, 33, 35, 37, 39, 41, 43, and combinations thereof. In a related aspect, the disclosure provides a nucleic acid sequence that is at least 90%, 91%, 92%, 93%, 94%, 95%, 96%, 97%, 98%, or 99% identical to a nucleic acid sequence selected from the group consisting of SEQ ID NOs 8, 10, 12, 14, 16, 18, 20, 22, 24, 26, 28, 30, 32, 34, 36, 38, 40, 42, and combinations thereof. In a related aspect, the disclosure provides an amino acid sequence that is at least 90%, 91%, 92%, 93%, 94%, 95%, 96%, 97%, 98%, or 99% identical to an amino acid sequence selected from the group consisting of SEQ ID NOs 9, 11, 13, 15, 17, 19, 21, 23, 25, 27, 29, 31, 33, 35, 37, 39, 41, 43, and combinations thereof.

In a related aspect, the disclosure provides a vector comprising any nucleic acid or any thioesterase mutant nucleotide sequence as described herein.

In a related aspect, the disclosure provides a bacterial cell comprising any vector as described herein. In a related aspect, the disclosure provides a bacterial cell comprising any nucleic acid as described herein. In a related aspect, the disclosure provides a bacterial cell comprising any thioesterase mutant nucleotide sequence as described herein. In a related aspect, the disclosure provides an *E. coli* cell comprising any vector as described herein. In a related aspect, the disclosure provides an *E. coli* cell comprising any nucleic acid as described herein. In a related aspect, the disclosure provides an *E. coli* cell comprising any thioesterase mutant nucleotide sequence as described herein.

In any of the embodiments disclosed herein, the bacterial cell can be an *E. coli* cell. In any of the embodiments disclosed herein, the *E. coli* cell can be from the DH5alpha, BL21, DH10B, MG1655 or BW25113 strains.

In any of the embodiments described herein, the method can further comprise detecting the end product. In any of the embodiments described herein, the end product can be detected by a variety of methods including but not limited to gas chromatography mass spectrometry, liquid chromatography mass spectrometry, or a biosensor (e.g., the biosensor described in U.S. Patent Pub. No. 2016/0122832).

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1: Application of the Method to Heterologous Enzyme AbTE and Endogenous Protein ACP A non-limiting exemplary application of this method was employed to engineer a heterologous bacterial acyl-ACP thioesterase for improved MCFA production in *Escherichia coli* by electrostatically matching the interface between the heterologous medium-chain *Acinetobacter baylyi* acyl-ACP thioesterase (AbTE) and the endogenous *E. coli* fatty acid ACP (*E. coli* AcpP).

Figure 1B:
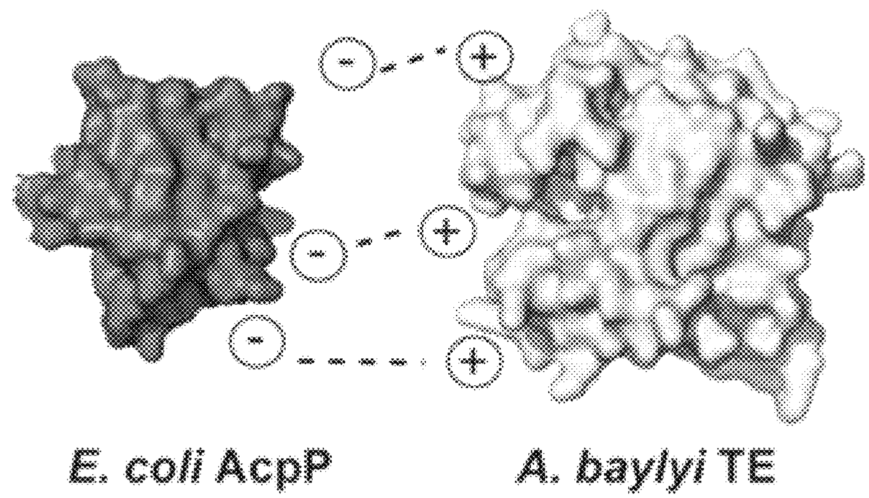

An exemplary application of this method, discussed in more detail below, involves the use of a natural medium-chain acyl-ACP TE as the engineering starting point in order to generate a TE variant with an almost exclusive MCFA product profile, potentially leading to higher MCFA yields. Engineering medium-chain acyl-ACP TEs has a unique set of challenges. First, medium-chain acyl-ACP-TEs are heterologous to *E. coli* and may have problems interfacing with the host machinery. Second, active site engineering of medium-chain acyl-ACP TEs may not prove to be as fruitful, as mutations may need to be much more subtle, potentially in the second shell, and overall more difficult to identify. The inventors hypothesized that engineering the interface of a heterologous medium chain TE to better complement the surface of *E. coli* fatty acid biosynthesis ACP (*E. coli* AcpP) may improve MCFA titers (FIG. 1). In Type II FAS, ACP is bound to the fatty acyl-chain and interacts with all the proteins in fatty acid biosynthesis. The fatty acyl chain is sequestered in the ACP hydrophobic core, and protein-protein interactions between the ACP and partner enzymes guide the maturing acyl chain from the ACP core and into each partner enzyme's active site. It is the selective binding of ACP to its enzyme partners, including the de novo FAS subunits, that enables efficient fatty acid biosynthesis. For instance, crosslinking studies show that *E. coli* Type II FAS ACP binds more selectively to its cognate *E. coli* Type II FAS ketoacid synthase (KS) than *Streptomyces maritimus* Type II polyketide synthase KS.

Here, the inventors engineered the medium-chain acyl-ACP AbT) to better interface with *E. coli* AcpP to improve MCFA production. First, the inventors docked *E. coli* AcpP with the endogenous *E. coli* TE 'TesA to identify potential contact residues involved in stabilizing the AcpP-'TesA interaction. Next, the inventors mutated the equivalent positions in AbTE to the amino acids found in *E. coli* 'TesA and measured its fatty acid profile. The inventors found that mutation of just two residues on the AbTE surface, G17 and A165 to arginines, improved MCFA titers more than 3-fold when compared to expression of AbTE wild type in *E. coli*. The inventors then showed that the AbTE mutations lead to new selective protein-protein interactions with *E. coli* ACP by performing NMR titrations between $^{15}$N-octanoyl-AcpP and the AbTEs.

Results

Screening Medium-Chain Acyl-ACP TEs and *E. coli* Hosts for MCFA Production.

Figure 2A:
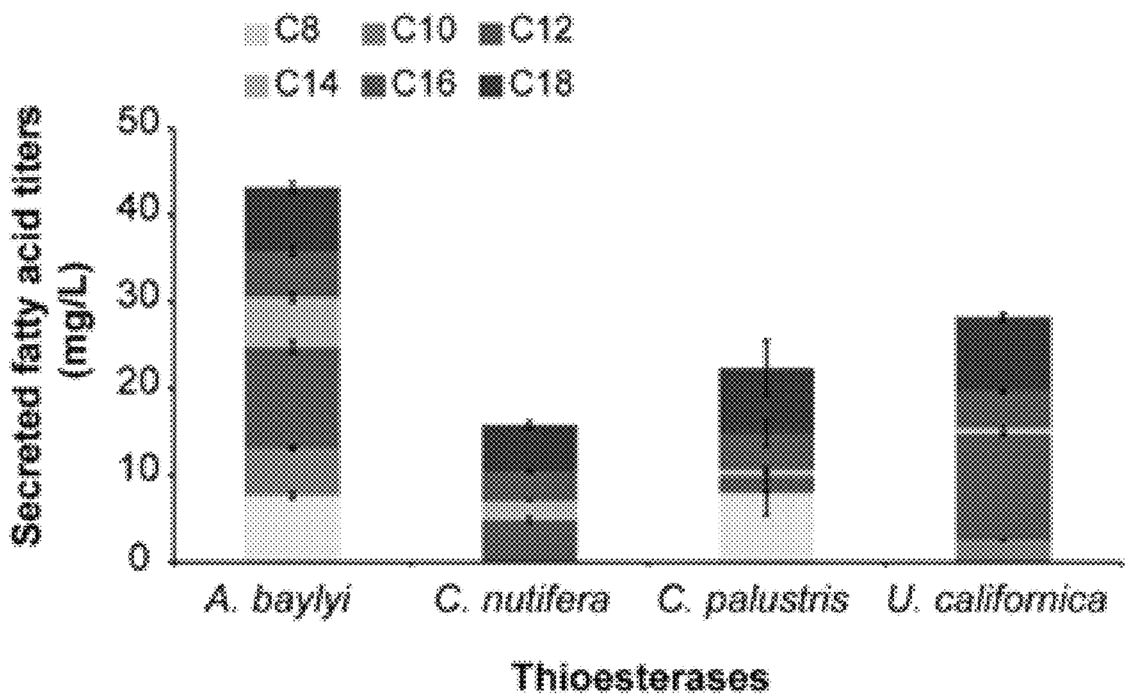

To identify the acyl-ACP TE that results in the highest secreted MCFA titers, the inventors expressed the bacterial TE from *Acinetobacter baylyi*, and the plant TEs from *Cocos nucifera, Cuphea palustris*, and *Umbellularia californica* in *E. coli* MG1655 (FIG. 2A). The percent sequence identity of these TEs to one another ranges from 15-17%; *A. baylyi* TE has the highest percent identity with *E. coli* 'TesA at 38% (Table 1). The inventors measured secreted fatty acids as they could be continuously extracted from the culture broth, overcoming issues with cell lysis, and potentially reducing the overall cost for MCFA production. AbTE results in the highest secreted MCFA titers at 29 mg/L, consisting of octanoic, decanoic and dodecanoic acid. *C nucifera* TE produced only dodecanoic acid at 5 mg/L, while *C. palustris* TE produced mostly octanoic acid at 8 mg/L. *U. californica* TE produced a mixture of decanoic and dodecanoic acid at 3 mg/L and 12 mg/L respectively. Given that AbTE resulted in the highest MCFA titers, the inventors selected this enzyme for further engineering.

TABLE 1

Percent sequence identity of thioesterases.

| | *E. coli* TesA | *Acinetobacter baylyi* TE |
|---|---|---|
| *E. coli* TesA | | 38.3% |
| *Acinetobacter baylyi* TE | 38.3% | |
| *Cocos nucifera* TE (plant) | 19.0% | 16.9% |
| *Umbellularia californica* TE (plant) | 21.1% | 14.7% |
| *Cuphea palustris* TE (plant) | 16.7% | 16.9% |

Figure 2B:
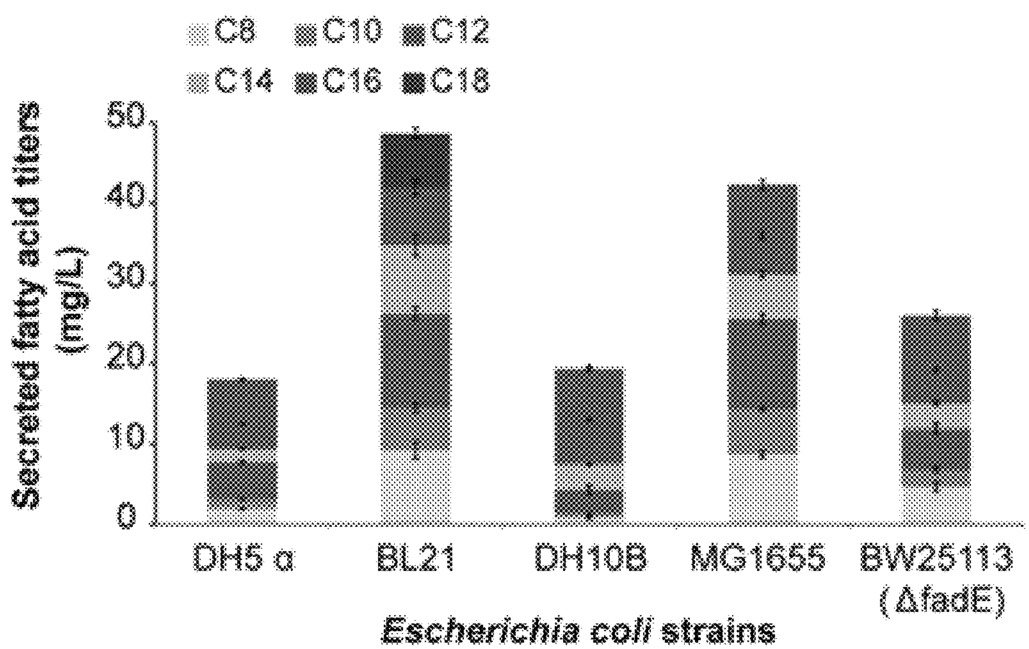

The *E. coli* genomic background has been shown to affect chemical production. The inventos expressed AbTE in five different *E. coli* hosts: DH5α, BL21, DH10B, MG1655, and BW25113 ΔfadE, and measured secreted MCFA titers. The inventors included the fadE deletion as it has been shown to improve fatty acid production in *E. coli*. Surprisingly, *E. coli* hosts BL21 and MG1655 resulted in the highest MCFA productions at 26 mg/L and BW25113 ΔfadE produced only 12 mg/L (FIG. 2B). Based on these results, the inventors moved forward with AbTE expressed in *E. coli* MG1655.

Engineering AbTE for Improved MCFA Titers.

Expression of the non-functional AbTE:S11A in *E. coli* produces only saturated long-chain (C14-C18) fatty acids (LCFA) due to the presence of endogenous long chain TEs. Expression of AbTE wild type (AbTE:WT) in *E. coli* produced ~29 mg/L of secreted MCFAs or ~52% of all secreted fatty acid chain lengths. When total fatty acids were measured, i.e. secreted fatty acids plus intracellular and membrane bound fatty acids, AbTE:WT expressed in *E. coli* produced ~48 mg/L of MCFAs, which is ~22% of total fatty acid chain lengths. While MCFA levels increased by 65% when taking into account intracellular and membrane bound fatty acids, LCFA levels increase more than 6-fold. Specifically, AbTE:WT produced octanoic, decanoic, and dodecanoic acid at 9 mg/L, 6, mg/L and 14 mg/L, respectively (FIG. 2A). In addition to saturated fatty acids, AbTE:WT also produced small levels of unsaturated C12-C16 fatty acids.

Figure 3:
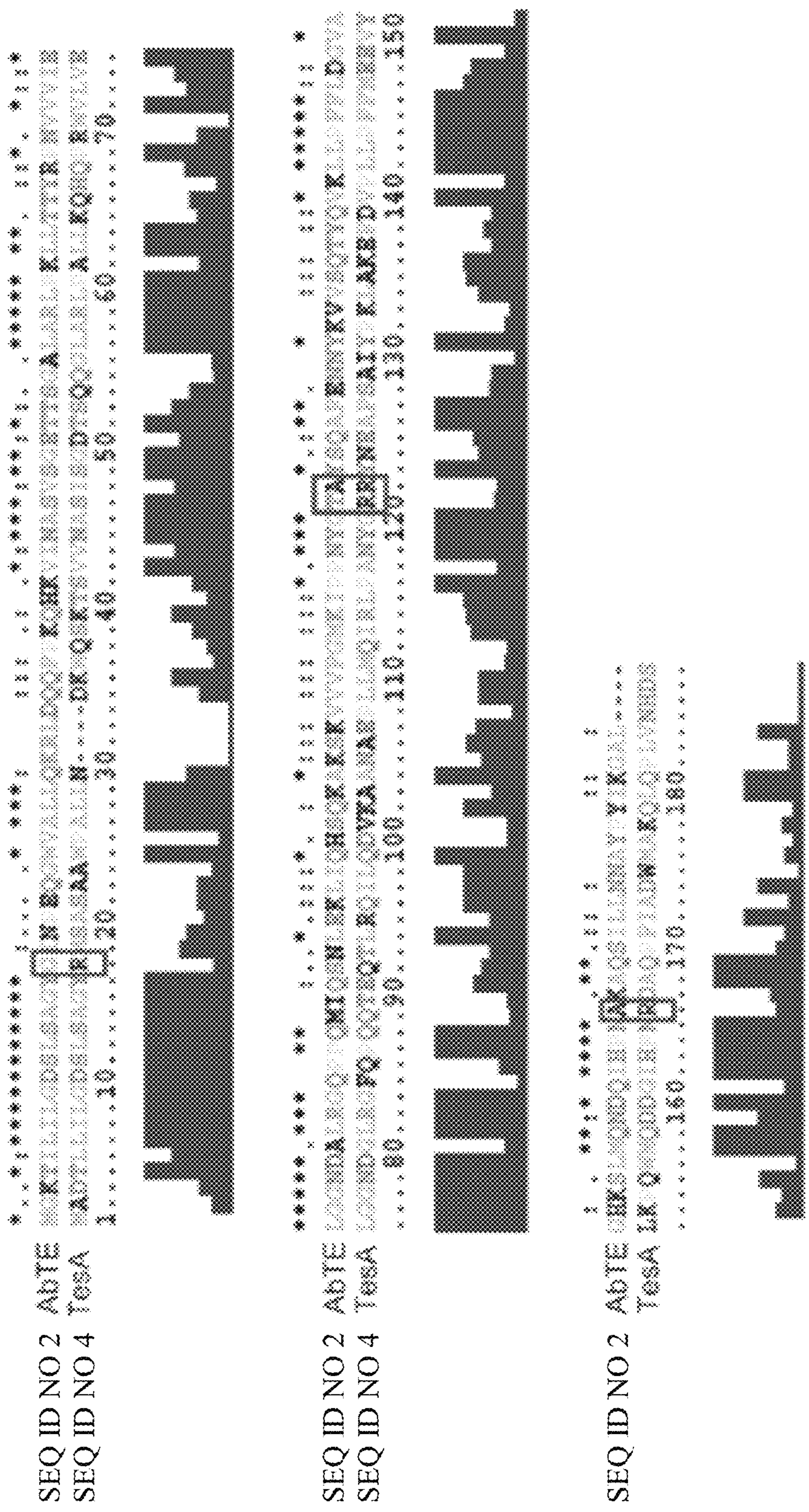
FIG. 3 shows the amino acid sequence alignment of AbTE wt and *E. coli* TesA with the signal peptide removed. Red boxes indicate amino acids targeted for mutagenesis.

To identify the interface between *E. coli* 'TesA and *E. coli* AcpP the inventors used ClusPro, which takes into account only the 'TesA-AcpP protein interactions to dock *E. coli* AcpP (PDB ID: 2FAE) and *E. coli* 'TesA bound to octanoic acid (PDB ID: 1U8U) (FIG. 2D). Using the model, the inventors identified eight positions on 'TesA that are potentially part of the AcpP-'TesA interface: Y15, R16, R77, N112, R115, R116, D153, and R160. Structural alignment of 'TesA with a AbTE homology model revealed that all positions except for R16 (AbTE: G17), R115 (AbTE: T120), R116 (AbTE: A121), D153 (AbTE: N158) and R160 (AbTE: A165) had the same amino acids in these two proteins (FIG. 2E, FIG. 3). Interestingly, four of the five amino acids that are different between 'TesA and AbTE are positively charged arginines, which could help stabilize the 'TesA-AcpP interaction as *E. coli* AcpP has a highly negative surface. While not wishing to be bound by theory, the inventors hypothesized that these interactions between AbTE and *E. coli* AcpP could be replicated in order to improve MCFA production.

Figure 6:
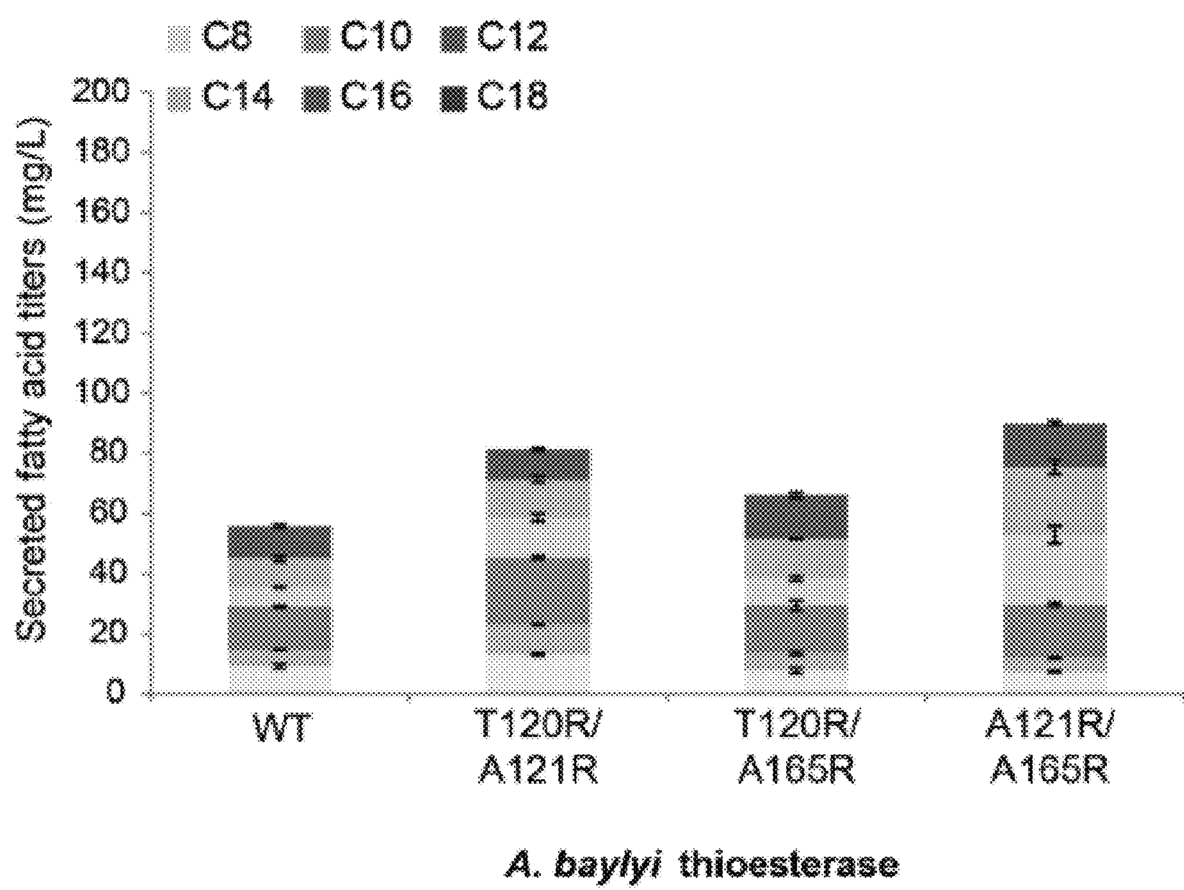
FIG. 6 shows secreted fatty acid production of *E. coli* expressing AbTE:WT, AbTE: T120R/A121R, AbTE: T120R/A165R, AbTE: A121R/A165R.

The inventors mutated positions 17, 120, 121, and 165 on AbTE to arginines to generate AbTE:G17R, AbTE:T120R, AbTE: A121R and AbTE:A165R, and measured their secreted fatty acid titers (FIG. 4A, FIGS. 5A-5D). Expression of AbTE:G17R in *E. coli* resulted in ~76 mg/L of secreted MCFAs, more than double the secreted MCFA titers from AbTE:WT. The MCFAs produced by AbTE:G17R accounted for ~74% of secreted fatty acids of all chain lengths. In particular, octanoic, decanoic and dodecanoic acid were produced at 30 mg/L, 18 mg/L and 28 mg/L, respectively. Expression of AbTE:A165R in *E. coli* resulted in slightly lower secreted MCFA titers than AbTE:WT. To determine if the effects of these mutations on MCFA titers were additive, we constructed all double mutants using AbTE:G17R as the scaffold. Expression of AbTE:G17R/A165R in *E. coli* resulted in ~98 mg/L of secreted MCFAs. This is a 29% increase in secreted MCFA titers when compared to expression of AbTE:G17R and a more than 3-fold in secreted MCFA titers when compared to AbTE:WT. Although AbTE:G17R/A165R secreted MCFA titers improved, the MCFA percentage was only 55% of secreted fatty acids of all chain lengths. The major constituent in the AbTE:G17R/A165R secreted MCFA profile was dodecanoic acid at 45 mg/L. The increase in secreted MCFA titer achieved by AbTE:G17R/A165R was unexpected as AbTE:A165R resulted in the lowest MCFA titers from all single mutants. Finally, the inventors generated the triple mutants using AbTE:G17R/A165R as the scaffold. At this stage, the inventors also mutated the fifth position on AbTE that varies from 'TesA, AbTE:N158D. This fifth position did not change the amino acid to a positively charged arginine, but to a negatively charged aspartate. Nevertheless, the aspartate could still form part of a stabilizing interaction. However, none of the triple mutants resulted in improved secreted MCFA titers. Of note, positions A121 and T120 are located on the other side of the AbTE binding pocket than G17 and A165. For completion, the inventors generated the remaining double mutants AbTE:T120R/A121R, AbTE:T120R/A121R, and AbTE:A121R/A165R and measured their secreted fatty acid titers (FIG. 6). While two of these double mutants produced comparable secreted MCFA titers to AbTE:WT, AbTE:T120R/A121R produced ~45 mg/L of secreted MCFAs. Taken together, AbTE:G17R/A165R results in the highest secreted MCFA titers (98 mg/L), yet AbTE:G17R has the highest percentage of secreted MCFAs (74%), a trend that holds true whether analyzing secreted or total fatty acids (Table 2).

TABLE 2

Saturated fatty acid percent composition produced by AbTE:WT and variants in *E. coli* strain MG1655 and M9 media.

| | Thioesterase | C8:0 (%) | C10:0 (%) | C12:0 (%) | C14:0 (%) | C16:0 (%) | C18:0 (%) |
|---|---|---|---|---|---|---|---|
| Supernatant | AbTE:WT | 16.5 | 10.5 | 25.2 | 11.5 | 17.1 | 19.2 |
| | AbTE:G17R | 29.3 | 17.5 | 27.3 | 4.7 | 9.1 | 12.1 |
| | AbTE:G17R/A165R | 18.5 | 11.7 | 25.4 | 21.2 | 14.2 | 9 |
| Total | AbTE:WT | 4.7 | 3.3 | 14.4 | 41.7 | 30.4 | 5.5 |
| | AbTE:G17R | 16.1 | 9.9 | 25.0 | 29.4 | 13.9 | 5.7 |
| | AbTE:G17R/A165R | 9.4 | 6.0 | 18.8 | 38.7 | 18.6 | 8.5 |

Extending Cultivation Time to Increase MCFA Titers.

Figure 4A:
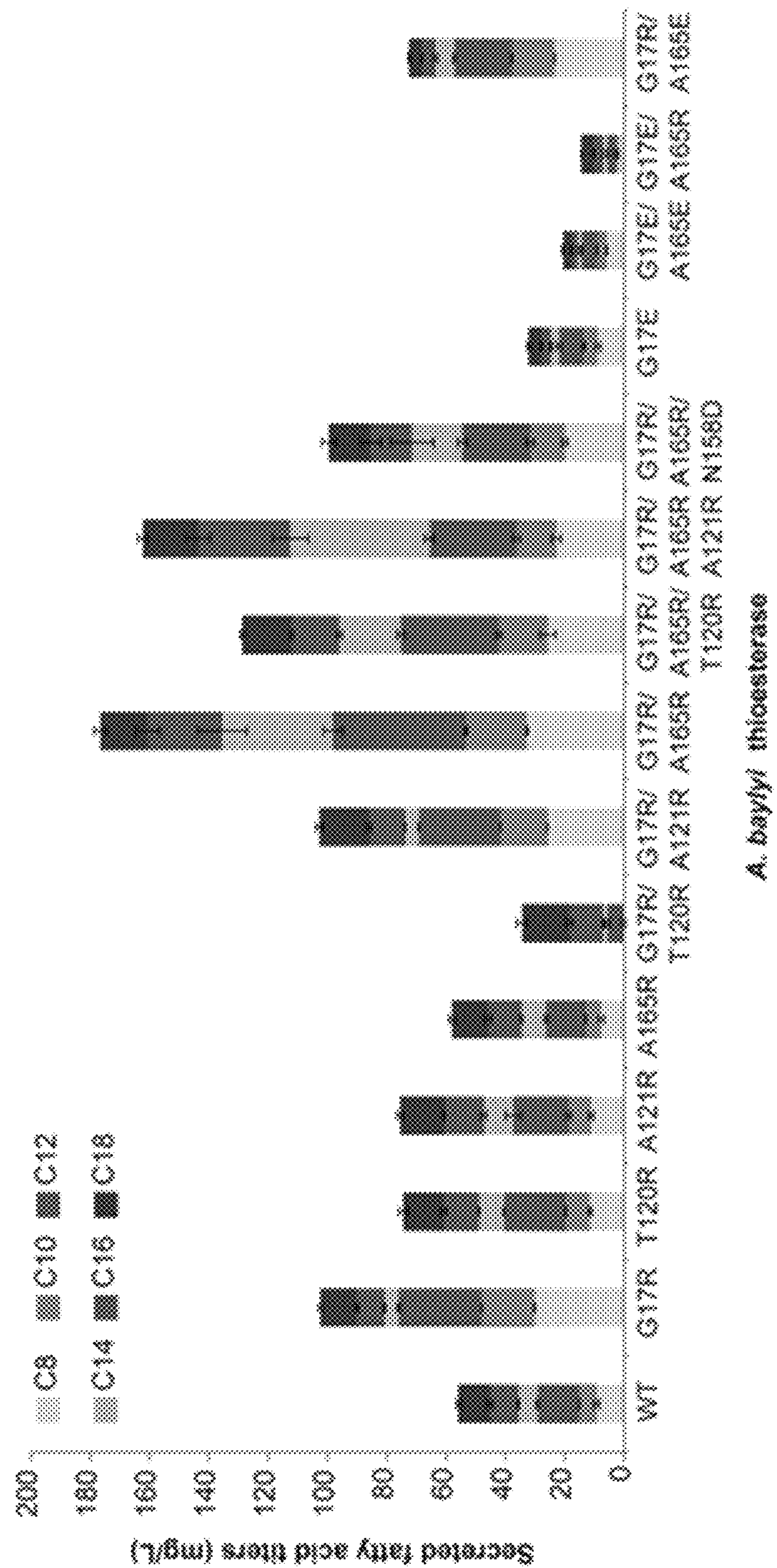
FIGS. 4A-4C show secreted fatty acid and protein levels of *E. coli* expressing *A. baylyi* TE (AbTE) and AbTE mutants.
Figure 4B:
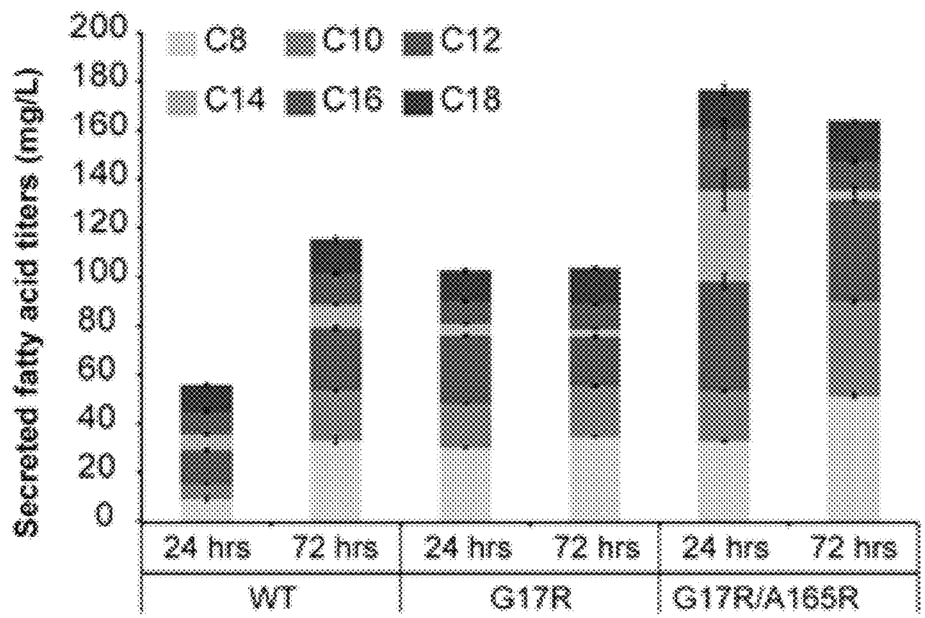

The inventors increased the cultivation time from 24 hrs to 72 hrs under the expectation that higher MCFA titers could accumulate during a longer cultivation period (FIG. 4B). When expressing AbTE:WT in *E. coli*, secreted MCFA titers almost tripled between 24 hrs and 72 hrs from ~29 mg/L to ~79 mg/L, jumping from being 52% to 69% of all secreted fatty acid chain lengths. Without wishing to be bound by theory, it is suggested that LCFAs are more likely to be ligated to CoA by endogenous FadD and enter the β-oxidation pathway, thus leading to a reduction of LCMA levels over time. Interestingly, cultivating *E. coli* expressing AbTE:G17R for 72 hrs did not result in any changes in MCFA titers. In contrast, the amount of secreted MCFAs in *E. coli* expressing AbTE:G17R/A165R increased from 98 mg/L to 131 mg/L when extending the cultivation time from 24 hrs to 72 hrs. This increase in MCFA titers increased the percentage of secreted MCFAs from 55% to 80%. Without wishing to be bound by theory, it is suggested that the low increase in MCFA titers observed with the AbTE mutants between 24 hrs and 72 hrs may be due to lost in activity after 24 hrs. It has been shown that adding solubility tags to heterologous proteins can increase their viability inside the host cell. However, attaching the maltose binding protein (MBP) tag to the N-terminus of the AbTE mutants, the terminus at the opposite end of the AcpP-AbTE interface, resulted only in LCFAs being produced, and no MCFAs were detected.

AbTE:G17R and AbTE:G17R/A165R Mode of Action.

Figure 4C:
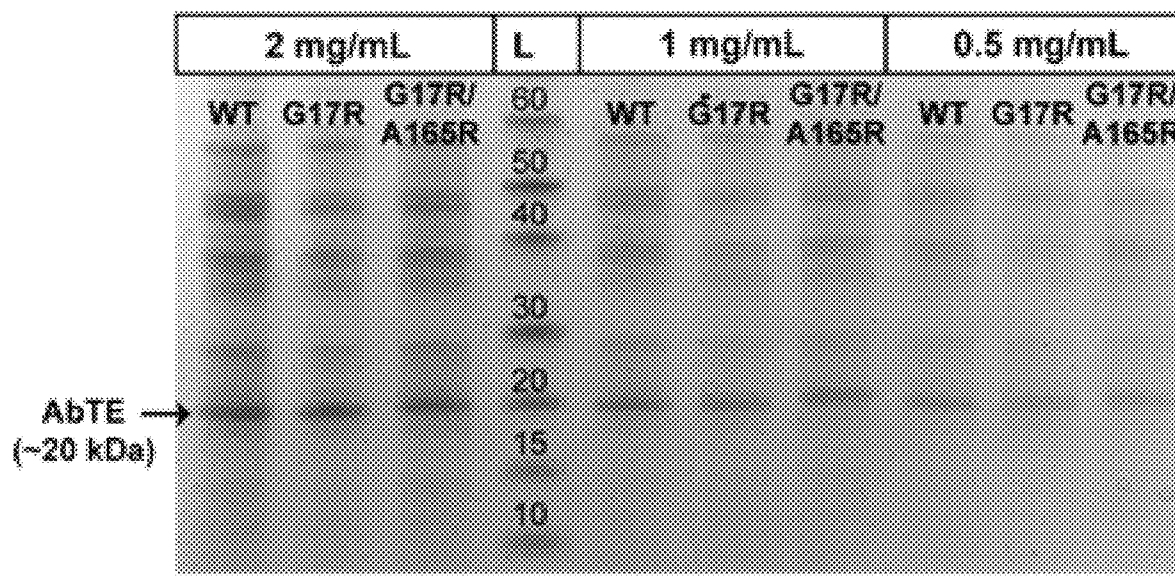
Figure 5A:
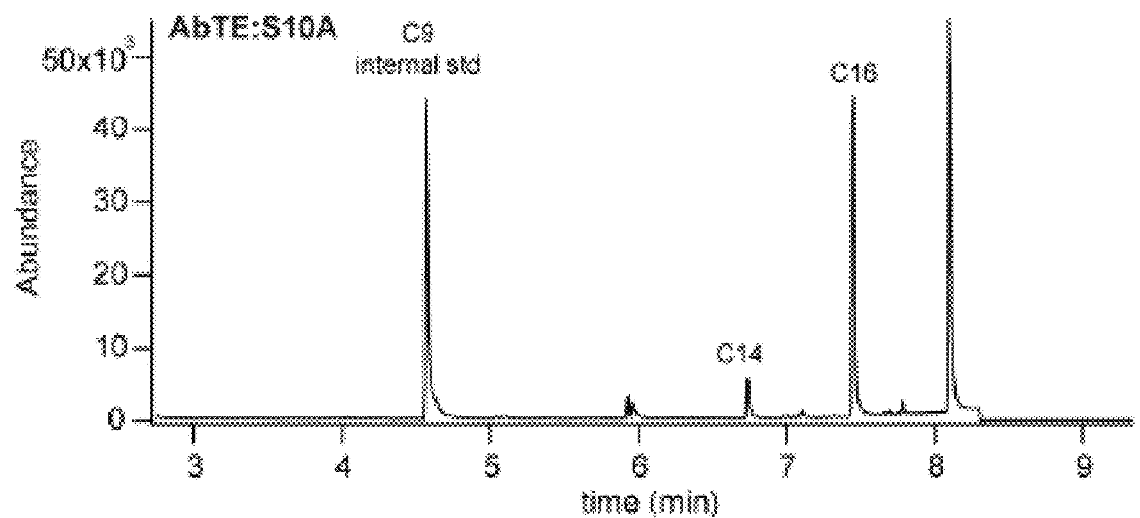
FIGS. 5A-5D show gas chromatograms of secreted fatty acids produced by *E. coli* expressing AbTE and AbTE variants.
Figure 5B:
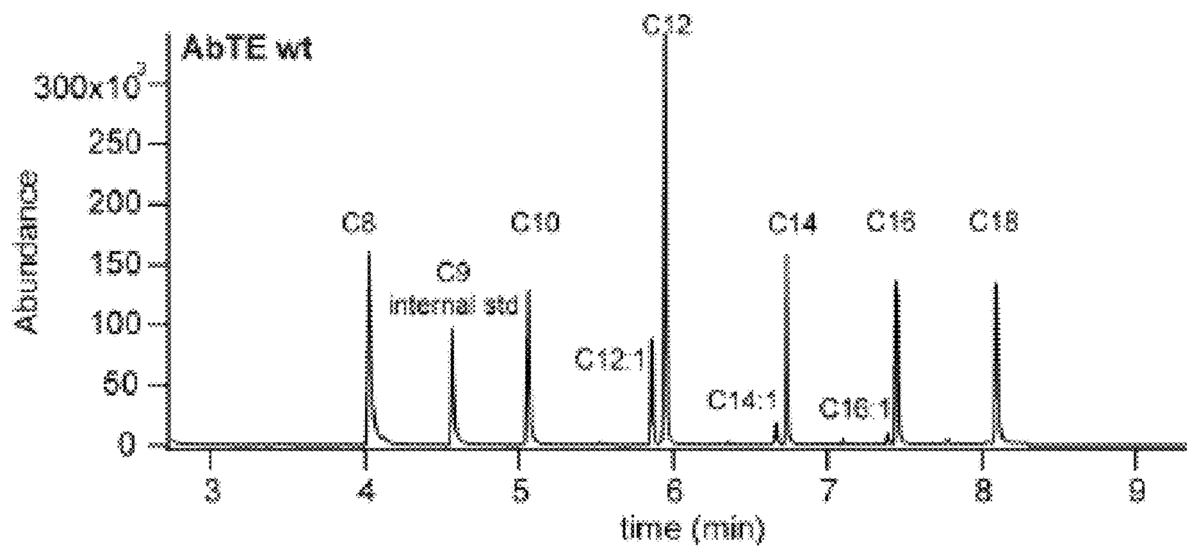
Figure 5C:
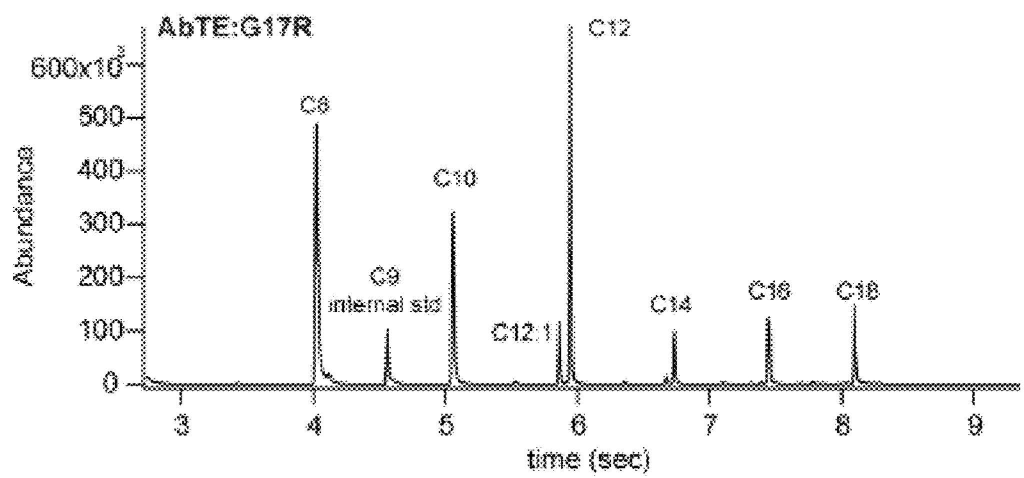
Figure 5D:
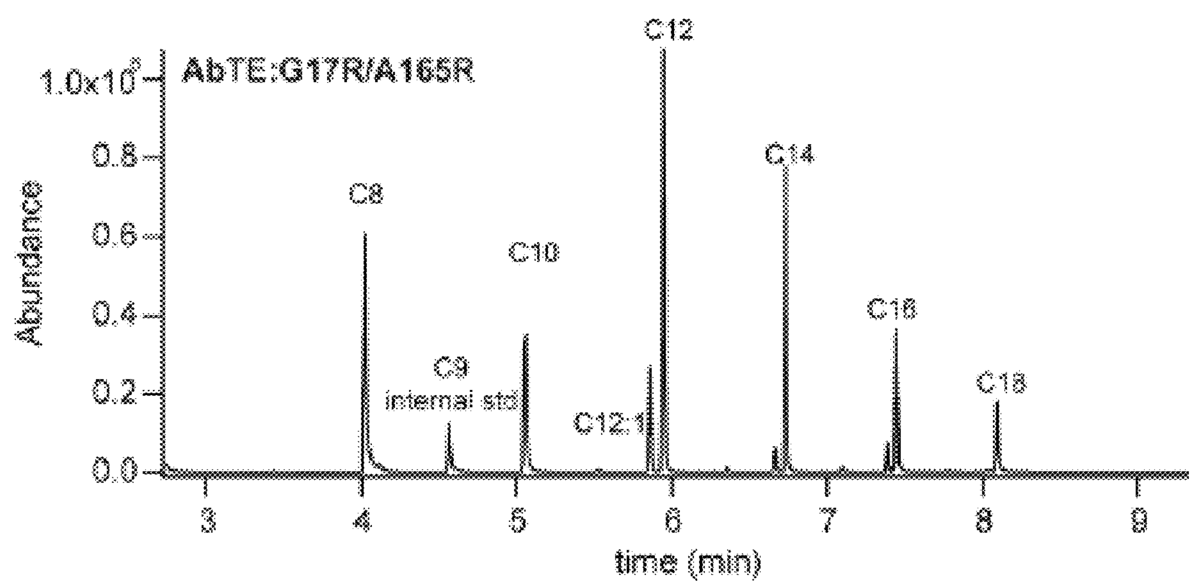

A possible reason for the improved MCFA profile of AbTE:G17R and AbTE:G17R/A165R when compared to AbTE:WT could be because these mutants are better expressed in *E. coli* relative to the other mutants. Positions 17 and 165 are located on the AbTE surface and it was hypothesized that mutating the small hydrophobic amino acids at these positions to positively charged arginines could improve solubility. A SDS-PAGE gel of *E. coli* expressing AbTE:WT, AbTE:G17R or AbTE:G17R/A165R showed comparable soluble expression of the three enzymes over 3 dilutions of cell lysate (FIG. 4C). In *E. coli*, arginines on the surface of FAS enzymes are essential for interaction with AcpP, which has a highly negatively charged surface. It has been shown that mutation of these arginines in FAS enzymes to negatively charged amino acids resulted in decreased interactions with ACP (FabA), decreased specific activity with ACP substrates (FabH, FabG), and decreased Kcat and increased $K_M$ with ACP substrates (FabI). If the newly introduced arginines on AbTE help stabilize AbTE-AcpP interactions, then it was hypothesized that mutating AbTE positions 17 and 165 to a negatively charged amino acid, such as glutamate, should disrupt *E. coli* AcpP interactions resulting in lower MCFA titers. In confirmation of this, *E. coli* expression of both the single AbTE:G17E and AbTE:G17E/A165E resulted in overall lower secreted fatty acid titers than AbTE:WT (FIG. 4A). Expression of AbTE:G17E and AbTE:G17E/A165E resulted in ~21 mg/L and 14 mg/L of secreted MCFAs, respectively, which was ~69% of secreted fatty acids of all chain lengths. Interestingly, AbTE:G17R/A165E resulted in ~57 mg/L of secreted MCFAs, which was ~79% of secreted fatty acids of all chain lengths. This favorable effect in secreted MCFAs or secreted fatty acids of all chain lengths is not seen in AbTE:G17E/A165R, making position 17 key in stabilizing AbTE-AcpP interactions. Taken together, the arginines on the AbTE surface do not affect the protein expression in *E. coli*, and enhance AbTE's interaction with *E. coli* AcpP.

Discussion

The inventors engineered the surface of a heterologous enzyme (AbTE) to better couple to an endogenous *E. coli* enzyme (AcpP) to increase chemical titers (MCFAs). Replacement of two small nonpolar residues on the AbTE surface predicted to contact *E. coli* AcpP, which has a highly negatively charged surface, with positively charged arginines, the amino acid found at the equivalent positions in *E. coli* 'TesA, resulted in more than 3-fold improvement in secreted MCFA titers. Replacing the small nonpolar residues of the AbTE surface with negatively charged glutamate resulted in lower overall secreted fatty acid titers. It is suggested that improving the interface between AbTE and AcpP enables AbTE to more efficiently accept medium chain fatty acyl-ACPs, thus improving MCFA titers. The experiments above showed that the improvement in MFCA titers was due to improved electrostatic interactions between AbTE mutants and AcpP rather than the expression levels of the AbTE mutants.

In the future, engineering the interface of heterologous proteins to better match the interface of host enzymes could be applied to more distantly related proteins, such as plant TEs. Such an approach may prove even more beneficial for more distantly related enzymes that may only marginally interact with endogenous host proteins. The recently determined structure of *U. californica* TE should assist with the identification of plant TE-AcpP interactions. In addition to MCFA production, the matching interface strategy could also be applied to medium-chain methyl ketone production by better coupling *E. coli* AcpPs to heterologous 0-ketoacyl-ACP TEs, such one from *Solanum habrochaites* (ShMKS2).

Methods

Homology Model and Docking.

AbTE homology mode was generated using Phyre2 intensive mode. The mode for 181 out of the 183 residues (99%) was modeled at >90% confidence. For docking *Escherichia coli* acyl-carrier protein (ACP, PDB ID: 2FAE, chain A) onto *E. coli* tesA (PDB ID: 1U8U) ClusPro was used. The 9 balanced models were analyzed using PyMol used to deduce the most likely ACP-tesA interactions. Structural alignment of TesA with AbTE was used to identify the ACP-AbTE interactions.

AbTE Mutant Generation.

Site-directed mutagenesis was performed using the QuikChange protocol with some modifications. PCR reaction: 0.8 ng/μL of template, 2.5 ng/μL of each primer, 1× iProof HF polymerase buffer, 0.02 U/L iProof polymerase (BioRad), 0.5 mM dNTPs to 50 μL final volume. Thermocycler protocol: 95° C. 1 min, 17 cycles: [95° C. 50 sec, 60° C. 50 sec, 72° C. 2 min 30 sec], 72° C. 7 min. DpnI (1 μL) was added to PCR reaction and incubated at 37° C. for 1 hour and heat inactivated at 65° C. for 20 min. 10 μL of reaction was transformed into competent DH10B *E. coli* cells.

SDS-PAGE Gel of AbTE:WT and AbTE Variants.

Overnight cultures of PPY1331, PPY1333, PPY1340 were diluted 1:50 in 1 mL of M9 media (0.5% glucose, amp100) and grown at 37° C., 250 r.p.m., until reaching OD600=0.3-0.4. The cells were then induced with 500 μM of IPTG (500 mM stock) and grown at 30° C., 250 rpm for 24 hours. A 1 mL of sample was removed from the culture medium and centrifuged for 5 min at 7354 g. The pellet was resuspended in 200 μL PBS (Teknova cat #P0195), sonicated twice for 20 sec each, and centrifuged at 7354 g for 5 min. The A280 of the resulting supernatant was measured using the NanoDrop Lite (Thermo) to measure protein concentration The supernatants were diluted to a concentration of 2 mg/mL of total protein to a final volume of 20 μL. After addition of 4 μL of 6×SDS loading dye to the 20 μL of the supernatant, the samples were then heated at 95° C. for 15 min. 20 μL of each sample was loaded to the SDS-PAGE gel, which was run at 200 V for 50 min at 4° C., and stained with Coomassie Blue.

Plasmid Construction.

Non-codon optimized *Acinetobacter baylyi* TE (AbTE), *S. cerevisiae* codon-optimized *Cuphea palustris* TE (CpTE), *E. coli* codon-optimized *Umbellularia californica* TE (UcTE) were commercially synthesized and cloned under $P_{TRC}$ in pMB1-$P_{TRC}$-AgGPPS-$(GSG)_2$-AgPS (pSS185) between NcoI/XmaI to generate pMB1-$P_{TRC}$-AbTE (pSS192), pMB1-$P_{TRC}$-CpTE (pSS183), and pMB1-$P_{TRC}$-UcTE (pSS193). *S. cerevisiae* codon-optimized CnTE was amplified from pESC-LEU2-$P_{TEF1}$-$P_{HXT7}$-CnTE (pSS81) with primers SS455/SS456 and cloned under $P_{TRC}$ in pSS185 between NcoI/XmaI to generate pMB1-$P_{TRC}$-CnTE (pSS174). AbTE mutants were generated using QuikChange protocol with some modifications (see above). For protein expression, a C-terminal $His_6$-tag was introduced into AbTE:WT, AbTE:G17R and AbTE:G17R/A165R using primers TB1/TB2 and cloned into pET-28b (amplified using primers TB3/TB4) to generate pET-28b-AbTE:WT, pET-28b-AbTE:G17R, and pET-28b-AbTE:G17R/A165R.

AbTE and ACP Expression and Purification.

pET-AbTE:WT, pET-AbTE:G17R, and pET-AbTE:G17R/A165R were transformed in *E. coli* BL21 (DE3) and grown in the presence of 50 mg/L of kanamycin. Cells were induced with 1 mM IPTG at $OD_{600}$=0.8 and grown for 16 to 18 hours at 16° C. Cell pellets were resuspended in 50 mM Hepes (pH 7.4), 250 mM NaCl, and 10% glycerol before lysis by sonication and clarification at 22,000 rcf Clarified lysate was allowed to batch bind the Ni-NTA resin for 20 minutes followed by washing with buffer containing 25 mM imidazole. Final elution was performed with buffer containing 250 mM imidazole, followed by dialysis into 50 mM Tris buffer (pH 7.4), 150 mM NaCl and 10% glycerol. After concentration to ~2 mL, the enzymes were purified on a GE Superdex 200 gel filtration column and the fractions containing the desired protein were checked by UV trace and SDS PAGE before concentration. The same procedure was followed for the $^{15}$N-AcpP, however, AcpP was grown in 1 g $^{15}$N ammonium chloride, 4 g of $^{12}$C glucose, 1 L of M9 media, and 50 mg of kanamycin.

MCFA Production, Derivatization and Quantification.

MCFA Production:

Overnight cultures of *E. coli* MG1655 expressing AbTE: WT or AbTE variants were diluted 1:50 in 5 mL of M9 media (0.5% glucose, $amp^{100}$) and grown at 37° C., 250 r.p.m. until reaching an $OD_{600}$=0.3-0.4. The cells were then induced with 500 μM of IPTG (500 mM stock) and grown at 30° C., 250 r.p.m. for 24 or 72 hrs. Fatty acid analysis: For secreted fatty acids, *E. coli* cultures were vortexed for 3 sec, 600 μL of culture removed and centrifuged for 10 min at 7354 g. Next, 400 μL of the supernatant was removed for derivatization. For total fatty acids, 400 μL of culture was used for derivatization. Fatty acid derivatization: Fatty acids were derivatized to fatty acid methyl esters and analyzed via GC/MS as described previously with some modifications. To the 400 μL of sample, 50 μL of 10% (wt/vol) NaCl, 50 μL of glacial acetic acid, 20 μL of 90.5 mg/L nonanoic acid (internal standard), and 200 μL of ethyl acetate were added and the mixture was vortexed for 5 sec. The mixture was then centrifuged at 12,098 g for 10 min. Methyl esters were generated by mixing 100 μL of the ethyl acetate layer with 900 μL of a 30:1 mixture of methanol and 37% (vol/vol) HCl in a 2 mL microcentrifuge tube, vortexed for 5 sec, and incubated at 50° C. for 1 hr. After cooling to room temperature, 500 μL of water and 500 μL of hexanes were added. The mixture was vortexed for 5 sec, 100 μL of the hexane layer was taken and mixed with 400 μL of ethyl acetate for analysis via GC-MS. FAME quantification: The samples were analyzed using Agilent 7890A/Agilent 5975 MS detector using a DB-5MS column. The inlet temperature was set to 300° C., flow at 1 mL/min, the oven at 70° C. for 1 min, ramp at 30° C./min to 290° C., and held for 1 min at 290° C. Standard curves of C8-C18 fully saturated FAMEs (Alfa Aesar/TCI) were used for sample quantification.

| Sequence Information |
|---|
| SEQ ID NO 1 *Acinetobacter baylyi* acyl-ACP thioesterase (AbTE) DNA wildtype<br>ATGGGCAAAACCATTCTTATCTTAGGCGACAGTCTGAGTGCGGGTTATGGCATTAAC<br>CCCGAACAGGGCTGGGTCGCTTTATTACAAAAACGTCTGGATCAACAATTTCCCAAG<br>CAGCATAAAGTCATTAATGCCAGTGTAAGTGGGGAAACCACCAGTGGTGCTTTAGCT<br>CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGCACTGCCTATAGTCAGGCATTTGAAAATAATTATAAGGTAGT<br>GAGTCAAACATATCAGGTTAAGTTGTTGCCATTTTTTCTTGATGGTGTGGCTGGACA<br>CAAAAGTCTAATGCAAAATGACCAGATCCATCCAAATGCCAAAGCCCAGTCAATCT<br>TGCTAAATAACGCATACCCATATATTAAAGGCGCTTTATAA |
| SEQ ID NO 2 AbTE protein wildtype<br>MGKTILILGDSLSAGYGINPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>GTAYSQAFENNYKVVSQTYQVKLLPFFLDGVAGHKSLMQNDQIHPNAKAQSILLNNAY<br>PYIKGAL |
| SEQ ID NO 3 *E. coli* TesA DNA wildtype<br>ATGGCGGATACCCTGCTGATTCTGGGCGATAGCCTGAGCGCGGGCTATCGCATGAGC<br>GCGAGCGCGGCGTGGCCGGCGCTGCTGAACGATAAATGGCAGAGCAAAACCAGCGT<br>GGTGAACGCGAGCATTAGCGGCGATACCAGCCAGCAGGGCCTGGCGCGCCTGCCGG<br>CGCTGCTGAAACAGCATCAGCCGCGCTGGGTGCTGGTGGAACTGGGCGGCAACGAT<br>GGCCTGCGCGGCTTTCAGCCGCAGCAGACCGAACAGACCCTGCGCCAGATTCTGCA<br>GGATGTGAAAGCGGCGAACGCGGAACCGCTGCTGATGCAGATTCGCCTGCCGGCGA<br>ACTATGGCCGCCGCTATAACGAAGCGTTTAGCGCGATTTATCCGAAACTGGCGAAA<br>GAATTTGATGTGCCGCTGCTGCCGTTTTTTATGGAAGAAGTGTATCTGAAACCGCAG<br>TGGATGCAGGATGATGGCATTCATCCGAACCGCGATGCGCAGCCGTTTATTGCGGAT<br>TGGATGGCGAAACAGCTGCAGCCGCTGGTGAACCATGATAGC |
| SEQ ID NO 4 *E. coli* TesA protein wildtype<br>MADTLLILGDSLSAGYRMSASAAWPALLNDKWQSKTSVVNASISGDTSQQGLARL<br>PALLKQHQPRWVLVELGGNDGLRGFQPQQTEQTLRQILQDVKAANAEPLL<br>MQIRLPANYGRRYNEAFSAIYPKLAKEFDVPLLPFFMEEVYLKPQWMQDD<br>GIHPNRDAQPFIADWMAKQLQPLVNHDS |

-continued

| Sequence Information |
|---|

SEQ ID NO 5 *Cocos nucifera* thioesterase FatB3
ATGTTGCCAGATTGGTCTATGTTGTTGGCTGCTATTAGAACCATTTTCTCCGCTGCTG
AGAAGCAATGGACTTTGCTCGATTCTAAGAAGCGAGGTGCTGATGCTGTTGCTGATG
CTTCTGGTGTTGGTAAGATGGTTAAGAATGGCTTGGTCTACAGACAGAACTTCTCCA
TTAGATCCTACGAAATTGGTGTTGATAAGAGAGCTTCCGTTGAGGCTTTGATGAATC
ATTTCCAAGAAACTTCTTTGAATCATTGTAAGTGTATTGGTTTGATGCATGGTGGTTT
CGGTTGTACTCCAGAAATGACTAGAAGAAATTTGATTTGGGTTGTTGCTAAGATGTT
GGTTCATGTTGAAAGATACCCCTGGTGGGGTGATGTTGTTCAAATTAATACTTGGAT
TTCTTCTTCTGGTAAGAATGGTATGGGTAGAGATTGGCATGTTCATGATTGTCAAAC
TGGTTTGCCAATTATGAGAGGTACTTCTGTTTGGGTTATGATGGATAAGCATACTAG
AAGATTGTCTAAGTTGCCAGAAGAAGTTAGAGCTGAAATTACTCCATTCTTCTCTGA
AAGAGATGCTGTTTTGGATGATAATGGTAGAAAGTTGCCAAAGTTCGATGACGATTC
TGCTGCTCATGTTAGAAGAGGTTTGACTCCAAGATGGCATGATTTCGATGTTAATCA
ACATGTTAATAATGTTAAGTACGTTGGTTGGATTTTGGAATCTGTTCCAGTTTGGATG
TTGGATGGTTACGAGGTTGCTACTATGTCTTTGGAGTACAGAAGAGAGTGTAGAATG
GATTCTGTTGTTCAATCTTTGACTGCTGTTTCTTCTGATCATGCTGATGGTTCTCCAAT
TGTTTGTCAACATTTGTTGAGATTGGAAGATGGTACTGAAATTGTTAGAGGTCAAAC
TGAATGGAGACCAAAGCAACAAGCTAGAGATTTGGGTAATATGGGTTTGCATCCAA
CTGAATCTAAATAA SEQ ID NO 6 *Cuphea palustris* thioesterase FatB1
ATGAGGCCAAACATGTTGATGGATTCCTTCGGCTTGGAAAGAGTCGTCCAAGATGGT
TTGGTCTTCAGACAATCCTTCTCCATTAGATCCTATGAAATTTGTGCTGATAGAACTG
CTTCCATTGAAACTGTCATGAACCATGTCCAAGAAACTTCCTTGAACCAATGTAAGT
CCATTGGTTTGTTGGATGATGGTTTCGGTAGATCCCCAGAAATGTGTAAGAGAGATT
TGATTTGGGTCGTCACTAGAATGAAGATTATGGTCAACAGATACCCAACTTGGGGTG
ATACTATTGAAGTCTCCACTTGGTTGTCTCAATCTGGTAAGATTGGTATGGGTAGAG
ATTGGTTGATTTCTGATTGTAACACTGGTGAAATTTTGGTCAGAGCTACTTCCGTCTA
CGCTATGATGAACCAGAAGACGAGAAGATTCTCCAAGTTGCCACATGAAGTCAGAC
AAGAATTTGCTCCACATTTCTTGGATTCCCCACCAGCTATTGAAGATAACGATGGTA
AGTTGCAAAAGTTCGATGTCAAGACTGGTGATTCCATTAGAAAGGGTTTGACTCCAG
GTTGGTACGATTTGGATGTCAACCAACATGTCTCTAACGTCAAGTACATTGGTTGGA
TTTTGGAATCTATGCCAACTGAAGTCTTGGAAACTCAAGAATTGTGTTCTTTGACTTT
GGAATACAGAAGAGAATGTGGTAGAGATTCTGTCTTGGAATCCGTCACTTCTATGGA
CCCATCTAAGGTCGGTGATAGATTCCAATACAGACATTTGTTGAGATTGGAAGATGG
TGCTGATATTATGAAGGGTAGAACTGAATGGAGACCAAAGAACGCTGGTACTAACG
GTGCTATTTCTACTGGTAAGACTTAA SEQ ID NO 7 *Umbellularia californica* thioesterase FatB2
ATGACTCTAGAGTGGAAACCGAAACCAAAACTGCCTCAACTGCTGGATGATCACTTC
GGTCTGCACGGTCTGGTGTTTCGTCGTACTTTCGCAATTCGTTCTTATGAAGTGGGTC
CAGATCGTTCTACCTCCATCCTGGCCGTCATGAACCACATGCAGGAAGCCACCCTGA
ATCACGCGAAATCTGTTGGTATCCTGGGTGATGGTTTCGGCACTACTCTGGAAATGT
CTAAACGTGACCTGATGTGGGTAGTGCGTCGCACCCACGTAGCAGTAGAGCGCTAC
CCTACTTGGGGTGACACTGTGGAAGTCGAGTGTTGGATTGGCGCGTCCGGTAACAAT
GGTATGCGTCGCGATTTTCTGGTCCGTGACTGTAAAACGGGCGAAATCCTGACGCGT
TGCACCTCCCTGAGCGTTCTGATGAACACCCGCACTCGTCGCCTGTCTACCATCCCG
GACGAAGTGCGCGGTGAGATCGGTCCTGCTTTCATCGATAACGTGGCAGTTAAAGA
CGACGAAATCAAGAAACTGCAAAAACTGAACGACTCCACCGCGGACTACATCCAGG
GCGGTCTGACTCCGCGCTGGAACGACCTGGATGTTAATCAGCATGTGAACAACCTGA
AATACGTTGCTTGGGTCTTCGAGACTGTGCCGGACAGCATTTTCGAAAGCCATCACA
TTTCCTCTTTTACTCTGGAGTACCGTCGCGAATGTACTCGCGACTCCGTTCTGCGCAG
CCTGACCACCGTAAGCGGCGGTTCTAGCGAGGCAGGTCTGGTCTGCGACCATCTGCT
GCAACTGGAAGGCGGCTCCGAAGTCCTGCGTGCGCGTACGGAGTGGCGTCCAAAGC
TGACGGATTCTTTCCGCGGCATCTCCGTAATTCCGGCGGAACCTCGTGTTTAA SEQ ID NO: 8 AbTE G17R DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGCCAAAGCCCAGTCAATCT
TGCTAAATAACGCATACCCATATATTAAAGGCGCTTTATAA SEQ ID NO 9 AbTE G17R protein
MGKTILILGDSLSAGYRINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNAKAQSILLNNAY
PYIKGAL -continued

| Sequence Information |
|---|

SEQ ID NO 10 AbTE T120R DNA
ATGGGCAAAACCATTCTTATCTTAGGCGACAGTCTGAGTGCGGGTTATGGCATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCAGGGCCTATAGTCAGGCATTTGAAAATAATTATAAGGTAG
TGAGTCAAACATATCAGGTTAAGTTGTTGCCATTTTTTCTTGATGGTGTGGCTGGACA
CAAAAGTCTAATGCAAAATGACCAGATCCATCCAAATGCCAAAGCCCAGTCAATCT
TGCTAAATAACGCATACCCATATATTAAAGGCGCTTTATAA

SEQ ID NO 11 AbTE T120R protein
MGKTILILGDSLSAGYGINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GRAYSQAFENNYKVVSQTYQVKLLPFFLDGVAGHKSLMQNDQIHPNAKAQSILLNNAY
PYIKGAL SEQ ID NO 12 AbTE A121R DNA
ATGGGCAAAACCATTCTTATCTTAGGCGACAGTCTGAGTGCGGGTTATGGCATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTAGATATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGCCAAAGCCCAGTCAATCT
TGCTAAATAACGCATACCCATATATTAAAGGCGCTTTATAA SEQ ID NO 13 AbTE A121R protein
MGKTILILGDSLSAGYGINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTRYSQAFENNYKVVSQTYQVKLLPFFLDGVAGHKSLMQNDQIHPNAKAQSILLNNAY
PYIKGAL SEQ ID NO 14 AbTE A165R DNA
ATGGGCAAAACCATTCTTATCTTAGGCGACAGTCTGAGTGCGGGTTATGGCATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATCGCAAAGCCCAGTCAATCT
TGCTAAATAACGCATACCCATATATTAAAGGCGCTTTATAA SEQ ID NO 15 AbTE A165R protein
MGKTILILGDSLSAGYGINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNRKAQSILLNNAY
PYIKGAL SEQ ID NO 16 AbTE G17R/A165R DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATCGCAAAGCCCAGTCAATCT
TGCTAAATAACGCATACCCATATATTAAAGGCGCTTTATAA SEQ ID NO 17 AbTE G17R/A165R protein
MGKTILILGDSLSAGYRINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNRKAQSILLNNAY
PYIKGAL SEQ ID NO 18 AbTE A121R/A165R DNA
ATGGGCAAAACCATTCTTATCTTAGGCGACAGTCTGAGTGCGGGTTATGGCATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT

| Sequence Information |
|---|
| CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGCACT**AGA**TATAGTCAGGCATTTGAAAATAATTATAAGGTAGT<br>GAGTCAAACATATCAGGTTAAGTTGTTGCCATTTTTTCTTGATGGTGTGGCTGGACA<br>CAAAAGTCTAATGCAAAATGACCAGATCCATCCAAAT**CGC**AAAGCCCAGTCAATCT<br>TGCTAAATAACGCATACCCATATATTAAAGGCGCTTTATAA |
| SEQ ID NO 19 AbTE A121R/A165R protein<br>MGKTILILGDSLSAGYGINPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>GT**R**YSQAFENNYKVVSQTYQVKLLPFFLDGVAGHKSLMQNDQIHPN**R**KAQSILLNNAY<br>PYIKGAL |
| SEQ ID NO 20 AbTE T120R/A165R DNA<br>ATGGGCAAAACCATTCTTATCTTAGGCGACAGTCTGAGTGCGGGTTATGGCATTAAC<br>CCCGAACAGGGCTGGGTCGCTTTATTACAAAAACGTCTGGATCAACAATTTCCCAAG<br>CAGCATAAAGTCATTAATGCCAGTGTAAGTGGGGAAACCACCAGTGGTGCTTTAGCT<br>CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGC**AGG**GCCTATAGTCAGGCATTTGAAAATAATTATAAGGTAG<br>TGAGTCAAACATATCAGGTTAAGTTGTTGCCATTTTTTCTTGATGGTGTGGCTGGACA<br>CAAAAGTCTAATGCAAAATGACCAGATCCATCCAAAT**CGC**AAAGCCCAGTCAATCT<br>TGCTAAATAACGCATACCCATATATTAAAGGCGCTTTATAA |
| SEQ ID NO 21 AbTE T120R/A165R protein<br>MGKTILILGDSLSAGYGINPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>G**R**AYSQAFENNYKVVSQTYQVKLLPFFLDGVAGHKSLMQNDQIHPN**R**KAQSILLNNAY<br>PYIKGAL |
| SEQ ID NO 22 AbTE G17R/A121R DNA<br>ATGGGCAAAACCATTCTTATCTTAGGCGACAGTCTGAGTGCGGGTTAT**AGA**ATTAAC<br>CCCGAACAGGGCTGGGTCGCTTTATTACAAAAACGTCTGGATCAACAATTTCCCAAG<br>CAGCATAAAGTCATTAATGCCAGTGTAAGTGGGGAAACCACCAGTGGTGCTTTAGCT<br>CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGCACT**AGA**TATAGTCAGGCATTTGAAAATAATTATAAGGTAGT<br>GAGTCAAACATATCAGGTTAAGTTGTTGCCATTTTTTCTTGATGGTGTGGCTGGACA<br>CAAAAGTCTAATGCAAAATGACCAGATCCATCCAAATGCCAAAGCCCAGTCAATCT<br>TGCTAAATAACGCATACCCATATATTAAAGGCGCTTTATAA |
| SEQ ID NO 23 AbTE G17R/A121R protein<br>MGKTILILGDSLSAGY**R**INPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>GT**R**YSQAFENNYKVVSQTYQVKLLPFFLDGVAGHKSLMQNDQIHPNAKAQSILLNNAY<br>PYIKGAL |
| SEQ ID NO 24 AbTE G17R/T120R DNA<br>ATGGGCAAAACCATTCTTATCTTAGGCGACAGTCTGAGTGCGGGTTAT**AGA**ATTAAC<br>CCCGAACAGGGCTGGGTCGCTTTATTACAAAAACGTCTGGATCAACAATTTCCCAAG<br>CAGCATAAAGTCATTAATGCCAGTGTAAGTGGGGAAACCACCAGTGGTGCTTTAGCT<br>CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGC**AGG**GCCTATAGTCAGGCATTTGAAAATAATTATAAGGTAG<br>GAGTCAAACATATCAGGTTAAGTTGTTGCCATTTTTTCTTGATGGTGTGGCTGGACA<br>CAAAAGTCTAATGCAAAATGACCAGATCCATCCAAATGCCAAAGCCCAGTCAATCT<br>TGCTAAATAACGCATACCCATATATTAAAGGCGCTTTATAA |
| SEQ ID NO 25 AbTE G17R/T120R protein<br>MGKTILILGDSLSAGY**R**INPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>G**R**AYSQAFENNYKVVSQTYQVKLLPFFLDGVAGHKSLMQNDQIHPNAKAQSILLNNAY<br>PYIKGAL |
| SEQ ID NO 26 T120R/A121R DNA<br>ATGGGCAAAACCATTCTTATCTTAGGCGACAGTCTGAGTGCGGGTTATGGCATTAAC<br>CCCGAACAGGGCTGGGTCGCTTTATTACAAAAACGTCTGGATCAACAATTTCCCAAG<br>CAGCATAAAGTCATTAATGCCAGTGTAAGTGGGGAAACCACCAGTGGTGCTTTAGCT<br>CGTTTACCCAAACTACTTACTACTTATCGACCTAATGTGGTGGTCATTGAGCTTGGTG<br>GTAATGATGCATTAAGAGGACAACCGCCTCAAATGATTCAAAGTAATCTGGAAAAA<br>TTAATCCAGCACAGCCAAAAGGCAAAATCTAAAGTCGTGGTGTTTGGAATGAAAAT<br>ACCACCAAATTATGGC**AGGAGA**TATAGTCAGGCATTTGAAAATAATTATAAGGTAG<br>TGAGTCAAACATATCAGGTTAAGTTGTTGCCATTTTTTCTTGATGGTGTGGCTGGACA |

| Sequence Information |
|---|

CAAAAGTCTAATGCAAAATGACCAGATCCATCCAAATGCCAAAGCCCAGTCAATCT
TGCTAAATAACGCATACCCATATATTAAAGGCGCTTTATAA

SEQ ID NO 27 T120R/A121R protein
MGKTILILGDSLSAGYGINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GRRYSQAFENNYKVVSQTYQVKLLPFFLDGVAGHKSLMQNDQIHPNAKAQSILLNNAY
PYIKGAL SEQ ID NO 28 AbTE S11A DNA
ATGGGCAAAACCATTCTTATCTTAGGCGACGCTCTGAGTGCGGGTTATGGCATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGCCAAAGCCCAGTCAATCT
TGCTAAATAACGCATACCCATATATTAAAGGCGCTTTATAA SEQ ID NO 29 AbTE S11A protein
MGKTILILGDALSAGYGINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNAKAQSILLNNAY
PYIKGAL SEQ ID NO 30 AbTE G17R/A165R/T120R DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCAGGGCCTATAGTCAGGCATTTGAAAATAATTATAAGGTAG
GAGTCAAACATATCAGGTTAAGTTGTTGCCATTTTTTCTTGATGGTGTGGCTGGACA
CAAAAGTCTAATGCAAAATGACCAGATCCATCCAAATCGCAAAGCCCAGTCAATCT
TGCTAAATAACGCATACCCATATATTAAAGGCGCTTTATAA SEQ ID NO 31 G17R/A165R/T120R protein
MGKTILILGDSLSAGYRINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GRAYSQAFENNYKVVSQTYQVKLLPFFLDGVAGHKSLMQNDQIHPNRKAQSILLNNAY
PYIKGAL SEQ ID NO 32 AbTE G17R/A165R/A121R DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTAGATATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATCGCAAAGCCCAGTCAATCT
TGCTAAATAACGCATACCCATATATTAAAGGCGCTTTATAA SEQ ID NO 33 G17R/A165R/A121R protein
MGKTILILGDSLSAGYRINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTRYSQAFENNYKVVSQTYQVKLLPFFLDGVAGHKSLMQNDQIHPNRKAQSILLNNAY
PYIKGAL SEQ ID NO 34 AbTE G17R/A165R/N158D DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAGATGACCAGATCCATCCAAATCGCAAAGCCCAGTCAATCT
TGCTAAATAACGCATACCCATATATTAAAGGCGCTTTATAA -continued

| Sequence Information |
|---|

SEQ ID NO 35 AbTE G17R/A165R/N158D protein
MGKTILILGDSLSAGYRINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQDDQIHPNRKAQSILLNNAY
PYIKGAL SEQ ID NO 36 AbTE G17E DNA
ATGGGCAAAACCATTCTTATCTTAGGCGACAGTCTGAGTGCGGGTTATGAAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGCCAAAGCCCAGTCAATCT
TGCTAAATAACGCATACCCATATATTAAAGGCGCTTTATAA SEQ ID NO 37 AbTE G17E protein
MGKTILILGDSLSAGYEINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNAKAQSILLNNAY
PYIKGAL SEQ ID NO 38 AbTE G17E/A165E DNA
ATGGGCAAAACCATTCTTATCTTAGGCGACAGTCTGAGTGCGGGTTATGAAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGAAAAAGCCCAGTCAATCT
TGCTAAATAACGCATACCCATATATTAAAGGCGCTTTATAA SEQ ID NO 39 AbTE G17E/A165E protein
MGKTILILGDSLSAGYEINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNEKAQSILLNNAY
PYIKGAL SEQ ID NO 40 AbTE G17E/A165R DNA
ATGGGCAAAACCATTCTTATCTTAGGCGACAGTCTGAGTGCGGGTTATGAAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATCGCAAAGCCCAGTCAATCT
TGCTAAATAACGCATACCCATATATTAAAGGCGCTTTATAA SEQ ID NO 41 AbTE G17E/A165R protein
MGKTILILGDSLSAGYEINPEQGWVALLQKRLDQQFPKQHKVINASVSGETTSGALARL
PKLLTTYRPNVVVIELGGNDALRGQPPQMIQSNLEKLIQHSQKAKSKVVVFGMKIPPNY
GTAYSQAFENNYKVVSQTYQVKLLPFFLDGVAGHKSLMQNDQIHPNRKAQSILLNNAY
PYIKGAL SEQ ID NO 42 AbTE G17R/A165E DNA
ATGGGCAAAACCATTCTTATCTTAGGCGACAGTCTGAGTGCGGGTTATAGAATTAAC
CCCGAACAGGGCTGGGTCGCTTTATTACAAAAACGTCTGGATCAACAATTTCCCAAG
CAGCATAAAGTCATTAATGCCAGTGTAAGTGGGGAAACCACCAGTGGTGCTTTAGCT
CGTTTACCCAAACTACTTACTACTTATCGACCTAATGTGGTGGTCATTGAGCTTGGTG
GTAATGATGCATTAAGAGGACAACCGCCTCAAATGATTCAAAGTAATCTGGAAAAA
TTAATCCAGCACAGCCAAAAGGCAAAATCTAAAGTCGTGGTGTTTGGAATGAAAAT
ACCACCAAATTATGGCACTGCCTATAGTCAGGCATTTGAAAATAATTATAAGGTAGT
GAGTCAAACATATCAGGTTAAGTTGTTGCCATTTTTTCTTGATGGTGTGGCTGGACA
CAAAAGTCTAATGCAAAATGACCAGATCCATCCAAATGAAAAAGCCCAGTCAATCT
TGCTAAATAACGCATACCCATATATTAAAGGCGCTTTATAA -continued

| Sequence Information |
| --- |
| SEQ ID NO 43 AbTE G17R/A165E protein<br>MGKTILILGDSLSAGY**R**INPEQGWVALLQKRLDQQFPKQHKVINASVSGETTSGALARL<br>PKLLTTYRPNVVVIELGGNDALRGQPPQMIQSNLEKLIQHSQKAKSKVVVFGMKIPPNY<br>GTAYSQAFENNYKVVSQTYQVKLLPFFLDGVAGHKSLMQNDQIHPN**E**KAQSILLNNAY<br>PYIKGAL |

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present disclosure will be limited only by the appended claims and equivalents thereof. The scope of the disclosure is therefore indicated by the following claims, rather than the foregoing description and above-discussed embodiments, and all changes that come within the meaning and range of equivalents thereof are intended to be embraced therein.

The invention claimed is:

1. A method for generating a thioesterase mutant comprising:

selecting a heterologous thioesterase for mutation based at least in part on a desired end product that is produced by the heterologous thioesterase;

identifying amino acids on the heterologous thioesterase that form an interacting surface with *E. coli* AcpP, are involved in stabilizing the interaction, and are suitable for mutation;

mutagenizing the identified amino acids of the heterologous thioesterase by introducing substitutions into a nucleic acid comprising the heterologous thioesterase nucleotide sequence; and expressing the nucleic acid comprising the mutated heterologous thioesterase nucleotide sequence in a bacterial cell to produce a heterologous thioesterase mutant, wherein the heterologous thioesterase mutant comprises an amino acid sequence that is at least 90% identical to an amino acid sequence selected from the group consisting of SEQ ID NOs 9, 11, 13, 15, 17, 19, 21, 23, 25, 27, 29, 31, 33, 35, 37, 39, 41, 43, and wherein the bacterial cell expressing the heterologous thioesterase mutant has an improved medium-chain fatty acid titer production compared to a bacterial cell expressing a wildtype heterologous thioesterase nucleotide sequence.

2. The method of claim 1, wherein the step of identifying amino acids comprises one or more of:

performing modeling to identify amino acids in an interacting surface between the AcpP protein and an endogenous thioesterase protein;

performing structural homology modeling to align the heterologous thioesterase amino acid sequence with the AcpP amino acid sequence to identify a corresponding interacting surface on the heterologous thioesterase; and performing modeling to identify amino acids in an interacting surface between the AcpP protein and the heterologous thioesterase protein.

3. The method of claim 1, wherein the step of identifying amino acids comprises:

determining an interaction between an endogenous thioesterase protein and the AcpP protein;

identifying corresponding amino acid positions in the heterologous thioesterase amino acid sequence via a structural homology modeling with the endogenous thioesterase amino acid sequence; and determining which amino acid substitutions in the heterologous thioesterase amino acid sequence will result in a similar interaction with the AcpP protein.

4. The method of claim 3, wherein the interaction between the endogenous thioesterase protein and the AcpP protein is selected from the group consisting of covalent bonds and non-covalent bonds.

5. The method of claim 3, wherein the interaction between the endogenous thioesterase protein and the AcpP protein is a non-covalent bond selected from the group consisting of electrostatic interactions, Van der Waals forces, hydrogen bonds and hydrophobic bonds.

6. The method of claim 1, wherein the step of mutagenizing the identified amino acids of the heterologous thioesterase is a mutagenesis selected from the group consisting of site-directed mutagenesis, site saturation mutagenesis, loop swapping mutagenesis, and CRISPR mutagenesis.

7. The method of claim 1, wherein the step of expressing the nucleic acid comprising the mutated heterologous thioesterase nucleotide sequence comprises:

cloning the nucleic acid comprising the mutated heterologous thioesterase nucleotide sequence into an expression vector;

transforming the expression vector into an appropriate bacterial host;

inducing expression of the heterologous thioesterase mutant; and analyzing an amount or purity of the end product produced by the heterologous thioesterase mutant.

8. The method of claim 1 further comprising:

identifying heterologous thioesterase mutants that yield a high amount of the end product and/or a high purity of the end product compared to wildtype heterologous thioesterase; and introducing those substitutions into a nucleic acid comprising the heterologous thioesterase nucleotide sequence to provide a multiple mutant thioesterase nucleotide sequence by a method comprising the steps of:

identifying additional amino acids on the heterologous thioesterase mutant that form an interacting surface with the AcpP protein and are involved in stabilizing the thioesterase-AcpP interaction;

mutagenizing the identified additional amino acids of the heterologous thioesterase mutant by introducing additional substitutions into a nucleic acid comprising the heterologous thioesterase mutant nucleotide sequence to provide a multiple mutant heterologous thioesterase mutant nucleotide sequence; and expressing the nucleic acid comprising the multiple mutant heterologous thioesterase mutant nucleotide sequence in a bacterial cell.

* * * * *

SEQUENCE LISTING

```
<160> NUMBER OF SEQ ID NOS: 43

<210> SEQ ID NO 1
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgggcaaaa ccattcttat cttaggcgac agtctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552


<210> SEQ ID NO 2
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
```

```
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 3
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atggcggata ccctgctgat tctgggcgat agcctgagcg cgggctatcg catgagcgcg     60

agcgcggcgt ggccggcgct gctgaacgat aaatggcaga gcaaaaccag cgtggtgaac    120

gcgagcatta gcggcgatac cagccagcag ggcctggcgc gcctgccggc gctgctgaaa    180

cagcatcagc cgcgctgggt gctggtggaa ctgggcggca acgatggcct gcgcggcttt    240

cagccgcagc agaccgaaca gaccctgcgc cagattctgc aggatgtgaa agcggcgaac    300

gcggaaccgc tgctgatgca gattcgcctg ccggcgaact atggccgccg ctataacgaa    360

gcgtttagcg cgatttatcc gaaactggcg aaagaatttg atgtgccgct gctgccgttt    420

tttatggaag aagtgtatct gaaaccgcag tggatgcagg atgatggcat tcatccgaac    480

cgcgatgcgc agccgtttat tgcggattgg atggcgaaac agctgcagcc gctggtgaac    540

catgatagc                                                            549
```

<210> SEQ ID NO 4
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Ala Asp Thr Leu Leu Ile Leu Gly Asp Ser Leu Ser Ala Gly Tyr
1               5                   10                  15

Arg Met Ser Ala Ser Ala Ala Trp Pro Ala Leu Leu Asn Asp Lys Trp
            20                  25                  30

Gln Ser Lys Thr Ser Val Val Asn Ala Ser Ile Ser Gly Asp Thr Ser
        35                  40                  45
```

```
Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
    130                 135                 140

Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180
```

<210> SEQ ID NO 5
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atgttgccag attggtctat gttgttggct gctattagaa ccattttctc cgctgctgag     60

aagcaatgga ctttgctcga ttctaagaag cgaggtgctg atgctgttgc tgatgcttct    120

ggtgttggta agatggttaa gaatggcttg gtctacagac agaacttctc cattagatcc    180

tacgaaattg gtgttgataa gagagcttcc gttgaggctt tgatgaatca tttccaagaa    240

acttctttga atcattgtaa gtgtattggt ttgatgcatg gtggtttcgg ttgtactcca    300

gaaatgacta gaagaaattt gatttgggtt gttgctaaga tgttggttca tgttgaaaga    360

taccccctggt ggggtgatgt tgttcaaatt aatacttgga tttcttcttc tggtaagaat    420

ggtatgggta gagattggca tgttcatgat tgtcaaactg gtttgccaat tatgagaggt    480

acttctgttt gggttatgat ggataagcat actagaagat tgtctaagtt gccagaagaa    540

gttagagctg aaattactcc attcttctct gaaagagatg ctgttttgga tgataatggt    600

agaaagttgc caaagttcga tgacgattct gctgctcatg ttagaagagg tttgactcca    660

agatggcatg atttcgatgt taatcaacat gttaataatg ttaagtacgt tggttggatt    720

ttggaatctg ttccagtttg gatgttggat ggttacgagg ttgctactat gtctttggag    780

tacagaagag agtgtagaat ggattctgtt gttcaatctt tgactgctgt ttcttctgat    840

catgctgatg gttctccaat tgtttgtcaa catttgttga gattggaaga tggtactgaa    900

attgttagag gtcaaactga atggagacca aagcaacaag ctagagattt gggtaatatg    960

ggtttgcatc caactgaatc taaataa                                        987
```

<210> SEQ ID NO 6
<211> LENGTH: 882
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 6

```
atgaggccaa acatgttgat ggattccttc ggcttggaaa gagtcgtcca agatggtttg     60

gtcttcagac aatccttctc cattagatcc tatgaaattt gtgctgatag aactgcttcc    120

attgaaactg tcatgaacca tgtccaagaa acttccttga accaatgtaa gtccattggt    180

ttgttggatg atggtttcgg tagatcccca gaaatgtgta agagagattt gatttgggtc    240

gtcactagaa tgaagattat ggtcaacaga tacccaactt ggggtgatac tattgaagtc    300

tccacttggt tgtctcaatc tggtaagatt ggtatgggta gagattggtt gatttctgat    360

tgtaacactg gtgaaatttt ggtcagagct acttccgtct acgctatgat gaaccagaag    420

acgagaagat tctccaagtt gccacatgaa gtcagacaag aatttgctcc acatttcttg    480

gattccccac cagctattga agataacgat ggtaagttgc aaaagttcga tgtcaagact    540

ggtgattcca ttagaaaggg tttgactcca ggttggtacg atttggatgt caaccaacat    600

gtctctaacg tcaagtacat tggttggatt ttggaatcta tgccaactga agtcttggaa    660

actcaagaat tgtgttcttt gactttggaa tacagaagag aatgtggtag agattctgtc    720

ttggaatccg tcacttctat ggacccatct aaggtcggtg atagattcca atacagacat    780

ttgttgagat tggaagatgg tgctgatatt atgaagggta gaactgaatg gagaccaaag    840

aacgctggta ctaacggtgc tatttctact ggtaagactt aa                       882
```

<210> SEQ ID NO 7
<211> LENGTH: 906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atgactctag agtggaaacc gaaaccaaaa ctgcctcaac tgctggatga tcacttcggt     60

ctgcacggtc tggtgtttcg tcgtactttc gcaattcgtt cttatgaagt gggtccagat    120

cgttctacct ccatcctggc cgtcatgaac cacatgcagg aagccaccct gaatcacgcg    180

aaatctgttg gtatcctggg tgatggtttc ggcactactc tggaaatgtc taaacgtgac    240

ctgatgtggg tagtgcgtcg cacccacgta gcagtagagc gctaccctac ttggggtgac    300

actgtggaag tcgagtgttg gattggcgcg tccggtaaca atggtatgcg tcgcgatttt    360

ctggtccgtg actgtaaaac gggcgaaatc ctgacgcgtt gcacctccct gagcgttctg    420

atgaacaccc gcactcgtcg cctgtctacc atcccggacg aagtgcgcgg tgagatcggt    480

cctgctttca tcgataacgt ggcagttaaa gacgacgaaa tcaagaaact gcaaaaactg    540

aacgactcca ccgcggacta catccagggc ggtctgactc cgcgctggaa cgacctggat    600

gttaatcagc atgtgaacaa cctgaaatac gttgcttggg tcttcgagac tgtgccggac    660

agcattttcg aaagccatca catttcctct tttactctgg agtaccgtcg cgaatgtact    720

cgcgactccg ttctgcgcag cctgaccacc gtaagcggcg gttctagcga ggcaggtctg    780

gtctgcgacc atctgctgca actggaaggc ggctccgaag tcctgcgtgc gcgtacggag    840

tggcgtccaa agctgacgga ttctttccgc ggcatctccg taattccggc ggaacctcgt    900

gtttaa                                                               906
```

<210> SEQ ID NO 8
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atgggcaaaa ccattcttat cttaggcgac agtctgagtg cgggttatag aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552
```

<210> SEQ ID NO 9
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 10

<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgggcaaaa ccattcttat cttaggcgac agtctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcagg    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552
```

<210> SEQ ID NO 11
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Arg Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 12
<211> LENGTH: 552

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atgggcaaaa ccattcttat cttaggcgac agtctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

agatatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552
```

<210> SEQ ID NO 13
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Arg Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 14
<211> LENGTH: 552
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 14

```
atgggcaaaa ccattcttat cttaggcgac agtctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atcgcaaagc ccagtcaatc ttgctaaata acgcataccc atatattaaa    540

ggcgctttat aa                                                         552
```

<210> SEQ ID NO 15
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

<210> SEQ ID NO 16
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
atgggcaaaa ccattcttat cttaggcgac agtctgagtg cgggttatag aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atcgcaaagc ccagtcaatc ttgctaaata acgcataccc atatattaaa    540

ggcgctttat aa                                                         552
```

<210> SEQ ID NO 17
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

<210> SEQ ID NO 18
<211> LENGTH: 552
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 18

```
atgggcaaaa ccattcttat cttaggcgac agtctgagtg cgggttatgg cattaacccc     60
gaacagggct gggtcgcttt attacaaaaa cgtctggatc aacaatttcc caagcagcat    120
aaagtcatta atgccagtgt aagtggggaa accaccagtg gtgctttagc tcgtttaccc    180
aaactactta ctacttatcg acctaatgtg gtggtcattg agcttggtgg taatgatgca    240
ttaagaggac aaccgcctca aatgattcaa agtaatctgg aaaaattaat ccagcacagc    300
caaaaggcaa aatctaaagt cgtggtgttt ggaatgaaaa taccaccaaa ttatggcact    360
agatatagtc aggcatttga aaataattat aaggtagtga gtcaaacata tcaggttaag    420
ttgttgccat tttttcttga tggtgtggct ggacacaaaa gtctaatgca aaatgaccag    480
atccatccaa atcgcaaagc ccagtcaatc ttgctaaata acgcataccc atatattaaa    540
ggcgctttat aa                                                        552
```

<210> SEQ ID NO 19
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Arg Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

<210> SEQ ID NO 20
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
atgggcaaaa ccattcttat cttaggcgac agtctgagtg cgggttatgg cattaacccc     60
gaacagggct gggtcgcttt attacaaaaa cgtctggatc aacaatttcc caagcagcat    120
aaagtcatta atgccagtgt aagtggggaa accaccagtg gtgctttagc tcgtttaccc    180
aaactactta ctacttatcg acctaatgtg gtggtcattg agcttggtgg taatgatgca    240
ttaagaggac aaccgcctca aatgattcaa agtaatctgg aaaaattaat ccagcacagc    300
caaaaggcaa aatctaaagt cgtggtgttt ggaatgaaaa taccaccaaa ttatggcagg    360
gcctatagtc aggcatttga aaataattat aaggtagtga gtcaaacata tcaggttaag    420
ttgttgccat tttttcttga tggtgtggct ggacacaaaa gtctaatgca aaatgaccag    480
atccatccaa atcgcaaagc ccagtcaatc ttgctaaata acgcataccc atatattaaa    540
ggcgctttat aa                                                        552
```

<210> SEQ ID NO 21
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Arg Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

<210> SEQ ID NO 22
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atgggcaaaa ccattcttat cttaggcgac agtctgagtg cgggttatag aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

agatatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552
```

<210> SEQ ID NO 23
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Arg Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 24
<211> LENGTH: 551
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgggcaaaa ccattcttat cttaggcgac agtctgagtg cgggttatag aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcagg    360

gcctatagtc aggcatttga aaataattat aaggtaggag tcaaacatat caggttaagt    420

tgttgccatt ttttcttgat ggtgtggctg gacacaaaag tctaatgcaa aatgaccaga    480

tccatccaaa tgccaaagcc cagtcaatct tgctaaataa cgcataccca tatattaaag    540

gcgctttata a                                                         551
```

<210> SEQ ID NO 25
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Arg Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 26
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgggcaaaa ccattcttat cttaggcgac agtctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcagg    360

agatatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                        552
```

<210> SEQ ID NO 27
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Gly Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Arg Arg Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 28
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atgggcaaaa ccattcttat cttaggcgac gctctgagtg cgggttatgg cattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                        552
```

<210> SEQ ID NO 29
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Gly Lys Thr Ile Leu Ile Leu Gly Asp Ala Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 30
<211> LENGTH: 551
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
atgggcaaaa ccattcttat cttaggcgac agtctgagtg cgggttatag aattaacccc     60
```

```
gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcagg    360

gcctatagtc aggcatttga aaataattat aaggtaggag tcaaacatat caggttaagt    420

tgttgccatt ttttcttgat ggtgtggctg gacacaaaag tctaatgcaa aatgaccaga    480

tccatccaaa tcgcaaagcc cagtcaatct tgctaaataa cgcataccca tatattaaag    540

gcgctttata a                                                         551


<210> SEQ ID NO 31
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Arg Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180


<210> SEQ ID NO 32
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

atgggcaaaa ccattcttat cttaggcgac agtctgagtg cgggttatag aattaacccc     60
```

```
gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

agatatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atcgcaaagc ccagtcaatc ttgctaaata acgcataccc atatattaaa    540

ggcgctttat aa                                                        552
```

```
<210> SEQ ID NO 33
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Arg Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

```
<210> SEQ ID NO 34
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

atgggcaaaa ccattcttat cttaggcgac agtctgagtg cgggttatag aattaacccc     60

gaacagggct gggtcgcttt attacaaaaa cgtctggatc aacaatttcc caagcagcat    120
```

```
aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca agatgaccag    480

atccatccaa atcgcaaagc ccagtcaatc ttgctaaata acgcataccc atatattaaa    540

ggcgctttat aa                                                         552

<210> SEQ ID NO 35
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asp Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180


<210> SEQ ID NO 36
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

atgggcaaaa ccattcttat cttaggcgac agtctgagtg cgggttatga aattaacccc     60

gaacagggct gggtcgcttt attacaaaaa cgtctggatc aacaatttcc caagcagcat    120
```

```
aaagtcatta atgccagtgt aagtggggaa accaccagtg gtgctttagc tcgtttaccc    180

aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgccaaagc ccagtcaatc ttgctaaata acgcataccc atatattaaa    540

ggcgctttat aa                                                         552
```

<210> SEQ ID NO 37
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Gly Lys Thr Ile Leu Ile Leu Gly Asp Ser Leu Ser Ala Gly Tyr
1               5                   10                  15

Glu Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 38
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atgggcaaaa ccattcttat cttaggcgac agtctgagtg cgggttatga aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180
```

aaactactta ctacttatcg acctaatgtg gtggtcattg agcttggtgg taatgatgca 240
ttaagaggac aaccgcctca aatgattcaa agtaatctgg aaaaattaat ccagcacagc 300
caaaaggcaa aatctaaagt cgtggtgttt ggaatgaaaa taccaccaaa ttatggcact 360
gcctatagtc aggcatttga aaataattat aaggtagtga gtcaaacata tcaggttaag 420
ttgttgccat tttttcttga tggtgtggct ggacacaaaa gtctaatgca aaatgaccag 480
atccatccaa atgaaaaagc ccagtcaatc ttgctaaata acgcataccc atatattaaa 540
ggcgctttat aa 552

<210> SEQ ID NO 39
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Met Gly Lys Thr Ile Leu Ile Leu Gly Asp Ser Leu Ser Ala Gly Tyr
1               5                   10                  15

Glu Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Glu Lys Ala Gln Ser Ile Leu Leu Asn Asn Ala Tyr
                165                 170                 175

Pro Tyr Ile Lys Gly Ala Leu
            180
```

<210> SEQ ID NO 40
<211> LENGTH: 552
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
atgggcaaaa ccattcttat cttaggcgac agtctgagtg cgggttatga aattaacccc 60
gaacagggct gggtcgcttt attacaaaaa cgtctggatc aacaatttcc caagcagcat 120
aaagtcatta atgccagtgt aagtggggaa accaccagtg gtgctttagc tcgtttaccc 180

```
aaactactta ctacttatcg acctaatgtg gtggtcattg agcttggtgg taatgatgca    240

ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atcgcaaagc ccagtcaatc ttgctaaata acgcataccc atatattaaa    540

ggcgctttat aa                                                        552
```

```
<210> SEQ ID NO 41
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Lys Thr Ile Leu Ile Leu Gly Asp Ser Leu Ser Ala Gly Tyr
1               5                   10                  15

Glu Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Arg Lys Ala Gln Ser Ile Leu Leu Asn Asn Ala Tyr
                165                 170                 175

Pro Tyr Ile Lys Gly Ala Leu
            180
```

```
<210> SEQ ID NO 42
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

atgggcaaaa ccattcttat cttaggcgac agtctgagtg cgggttatag aattaacccc     60

gaacagggct gggtcgcttt attacaaaaa cgtctggatc aacaatttcc caagcagcat    120

aaagtcatta atgccagtgt aagtggggaa accaccagtg gtgctttagc tcgtttaccc    180

aaactactta ctacttatcg acctaatgtg gtggtcattg agcttggtgg taatgatgca    240
```

-continued

```
ttaagaggac aaccgcctca aatgattcaa agtaatctgg aaaaattaat ccagcacagc    300

caaaaggcaa aatctaaagt cgtggtgttt ggaatgaaaa taccaccaaa ttatggcact    360

gcctatagtc aggcatttga aaataattat aaggtagtga gtcaaacata tcaggttaag    420

ttgttgccat tttttcttga tggtgtggct ggacacaaaa gtctaatgca aaatgaccag    480

atccatccaa atgaaaaagc ccagtcaatc ttgctaaata acgcataccc atatattaaa    540

ggcgctttat aa                                                        552
```

```
<210> SEQ ID NO 43
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Lys Thr Ile Leu Ile Leu Gly Asp Ser Leu Ser Ala Gly Tyr
1               5                   10                  15

Arg Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Glu Lys Ala Gln Ser Ile Leu Leu Asn Asn Ala Tyr
                165                 170                 175

Pro Tyr Ile Lys Gly Ala Leu
            180
```